(12) United States Patent  
Cain

(10) Patent No.: US 10,071,266 B2  
(45) Date of Patent: *Sep. 11, 2018

(54) LESION GENERATION THROUGH BONE USING HISTOTRIPSY THERAPY WITHOUT ABERRATION CORRECTION

(71) Applicant: THE REGENTS OF THE UNIVERSITY OF MICHIGAN, Ann Arbor, MI (US)

(72) Inventor: Charles A. Cain, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 374 days.

This patent is subject to a terminal disclaimer.

(21) Appl. No.: 14/845,059

(22) Filed: Sep. 3, 2015

(65) Prior Publication Data

US 2015/0375015 A1 Dec. 31, 2015

Related U.S. Application Data

(63) Continuation of application No. 13/570,708, filed on Aug. 9, 2012, now Pat. No. 9,144,694.

(Continued)

(51) Int. Cl.
*A61N 7/00* (2006.01)
*A61N 7/02* (2006.01)
(Continued)

(52) U.S. Cl.
CPC ................. *A61N 7/00* (2013.01); *A61B 8/13* (2013.01); *A61B 17/320068* (2013.01);
(Continued)

(58) Field of Classification Search
CPC ........... A61B 2018/00642; A61B 2018/00702; A61B 17/320068; A62B 8/13;
(Continued)

(56) References Cited

U.S. PATENT DOCUMENTS 3,243,497 A 3/1966 Kendall et al.
3,679,021 A 7/1972 Goldberg et al.
(Continued)

FOREIGN PATENT DOCUMENTS

CN 102481164 A 5/2012
DE 3220751 A1 12/1983
(Continued)

OTHER PUBLICATIONS

Hobarth et al.; Color flow doppler sonography for extracorporal shock wave lithotripsy; Journal of Urology; 150(6); pp. 1768-1770; Dec. 1, 1993.

(Continued)

*Primary Examiner* — Michael Peffley  
(74) *Attorney, Agent, or Firm* — Shay Glenn LLP

(57) ABSTRACT

A medical imaging and therapy device is provided that may include any of a number of features. The device may include a Histotripsy transducer, a generator and controller configured to deliver Histotripsy energy from the transducer to target tissue, and an imaging system. In some embodiments, a method of treating tissue with Histotripsy energy comprises positioning a focus of a histotripsy transducer on a target tissue, delivering histotripsy energy from the histotripsy transducer through a bone aberrator, forming a histotripsy bubble cloud on the focus, and preventing the formation of secondary histotripsy bubble clouds without implementing an aberration correction algorithm.

15 Claims, 10 Drawing Sheets

Related U.S. Application Data

(60) Provisional application No. 61/521,986, filed on Aug. 10, 2011.

(51) Int. Cl.
*A61B 8/13* (2006.01)
*A61B 17/32* (2006.01)
*A61B 18/00* (2006.01)
*A61B 8/08* (2006.01)
*A61B 90/00* (2016.01)

(52) U.S. Cl.
CPC .............. *A61N 7/02* (2013.01); *A61B 8/0816* (2013.01); *A61B 2018/00642* (2013.01); *A61B 2018/00702* (2013.01); *A61B 2090/378* (2016.02); *A61N 2007/003* (2013.01); *A61N 2007/0039* (2013.01); *A61N 2007/0052* (2013.01)

(58) Field of Classification Search
CPC .. A62B 8/0816; A61N 7/02; A61N 2007/003; A61N 2007/0039; A61N 2007/0052
See application file for complete search history.

(56) References Cited

U.S. PATENT DOCUMENTS

| | | |
|---|---|---|
| 4,016,749 A | 4/1977 | Wachter |
| 4,024,501 A | 5/1977 | Herring et al. |
| 4,051,394 A | 9/1977 | Tieden |
| 4,117,446 A | 9/1978 | Alais |
| 4,269,174 A | 5/1981 | Adair |
| 4,277,367 A | 7/1981 | Madsen et al. |
| 4,351,038 A | 9/1982 | Alais |
| 4,406,153 A | 9/1983 | Ophir et al. |
| 4,440,025 A | 4/1984 | Hayakawa et al. |
| 4,453,408 A | 6/1984 | Clayman |
| 4,483,345 A | 11/1984 | Miwa |
| 4,549,533 A | 10/1985 | Cain et al. |
| 4,550,606 A | 11/1985 | Drost |
| 4,575,330 A | 3/1986 | Hull |
| 4,622,972 A | 11/1986 | Giebeler, Jr. |
| 4,625,731 A | 12/1986 | Quedens et al. |
| 4,641,378 A | 2/1987 | McConnell et al. |
| 4,669,483 A | 6/1987 | Hepp et al. |
| 4,689,986 A | 9/1987 | Carson et al. |
| 4,757,820 A | 7/1988 | Itoh |
| 4,791,915 A | 12/1988 | Barsotti et al. |
| 4,819,621 A | 4/1989 | Ueberle et al. |
| 4,829,491 A | 5/1989 | Saugeon et al. |
| 4,856,107 A | 8/1989 | Dory |
| 4,865,042 A | 9/1989 | Umemura et al. |
| 4,888,746 A | 12/1989 | Wurster et al. |
| 4,890,267 A | 12/1989 | Rudolph |
| 4,922,917 A | 5/1990 | Dory |
| 4,938,217 A | 7/1990 | Lele |
| 4,957,099 A | 9/1990 | Hassler |
| 4,973,980 A | 11/1990 | Howkins et al. |
| 4,984,575 A | 1/1991 | Uchiyama et al. |
| 4,991,151 A | 2/1991 | Dory |
| 4,995,012 A | 2/1991 | Dory |
| RE33,590 E | 5/1991 | Dory |
| 5,014,686 A | 5/1991 | Schafer |
| 5,065,751 A | 11/1991 | Wolf |
| 5,080,101 A | 1/1992 | Dory |
| 5,080,102 A | 1/1992 | Dory |
| 5,091,893 A | 2/1992 | Smith et al. |
| 5,092,336 A | 3/1992 | Fink |
| 5,097,709 A | 3/1992 | Masuzawa et al. |
| 5,111,822 A | 5/1992 | Dory |
| 5,143,073 A | 9/1992 | Dory |
| 5,143,074 A | 9/1992 | Dory |
| 5,150,711 A | 9/1992 | Dory |
| 5,158,070 A | 10/1992 | Dory |
| 5,158,071 A | 10/1992 | Umemura et al. |
| 5,163,421 A | 11/1992 | Bernstein et al. |
| 5,165,412 A | 11/1992 | Okazaki |
| 5,174,294 A | 12/1992 | Saito et al. |
| 5,209,221 A | 5/1993 | Riedlinger |
| 5,215,680 A | 6/1993 | D'Arrigo |
| 5,219,401 A | 6/1993 | Cathignol et al. |
| 5,230,340 A | 7/1993 | Rhyne |
| 5,295,484 A | 3/1994 | Marcus et al. |
| 5,316,000 A | 5/1994 | Chapelon et al. |
| 5,354,258 A | 10/1994 | Dory |
| 5,380,411 A | 1/1995 | Schlief |
| 5,409,002 A | 4/1995 | Pell |
| 5,431,621 A | 7/1995 | Dory |
| 5,435,311 A | 7/1995 | Umemura et al. |
| 5,443,069 A | 8/1995 | Schaetzle |
| 5,469,852 A | 11/1995 | Nakamura et al. |
| 5,474,071 A | 12/1995 | Chapelon et al. |
| 5,474,531 A | 12/1995 | Carter |
| 5,501,655 A | 3/1996 | Rolt et al. |
| 5,520,188 A | 5/1996 | Hennige et al. |
| 5,523,058 A | 6/1996 | Umemura et al. |
| 5,524,620 A | 6/1996 | Rosenschein |
| 5,540,909 A | 7/1996 | Schutt |
| 5,542,935 A | 8/1996 | Unger et al. |
| 5,558,092 A | 9/1996 | Unger et al. |
| 5,563,346 A | 10/1996 | Bartelt et al. |
| 5,566,675 A | 10/1996 | Li et al. |
| 5,573,497 A | 11/1996 | Chapelon |
| 5,580,575 A | 12/1996 | Unger et al. |
| 5,582,578 A | 12/1996 | Zhong et al. |
| 5,590,657 A | 1/1997 | Cain et al. |
| 5,601,526 A | 2/1997 | Chapelon et al. |
| 5,617,862 A | 4/1997 | Cole et al. |
| 5,648,098 A | 7/1997 | Porter |
| 5,666,954 A | 9/1997 | Chapelon et al. |
| 5,676,452 A | 10/1997 | Scholz |
| 5,676,692 A | 10/1997 | Sanghvi et al. |
| 5,678,554 A | 10/1997 | Hossack et al. |
| 5,694,936 A | 12/1997 | Fujimoto et al. |
| 5,695,460 A | 12/1997 | Siegel et al. |
| 5,717,657 A | 2/1998 | Ruffa |
| 5,724,972 A | 3/1998 | Petrofsky |
| 5,743,863 A | 4/1998 | Chapelon |
| 5,753,929 A | 5/1998 | Bliss |
| 5,759,162 A | 6/1998 | Oppelt et al. |
| 5,766,138 A | 6/1998 | Rattner |
| 5,769,790 A | 6/1998 | Watkins et al. |
| 5,797,848 A | 8/1998 | Marian et al. |
| 5,823,962 A | 10/1998 | Schaetzle et al. |
| 5,827,204 A | 10/1998 | Grandia et al. |
| 5,836,896 A | 11/1998 | Rosenschein |
| 5,849,727 A | 12/1998 | Porter et al. |
| 5,873,902 A | 2/1999 | Sanghvi et al. |
| 5,879,314 A | 3/1999 | Peterson et al. |
| 5,932,807 A | 8/1999 | Mallart |
| 5,947,904 A | 9/1999 | Hossack et al. |
| 6,001,069 A | 12/1999 | Tachibana et al. |
| 6,022,309 A | 2/2000 | Celliers et al. |
| 6,036,667 A | 3/2000 | Manna et al. |
| 6,088,613 A | 7/2000 | Unger |
| 6,093,883 A | 7/2000 | Sanghvi et al. |
| 6,113,558 A | 9/2000 | Rosenschein et al. |
| 6,126,607 A | 10/2000 | Whitmore, III et al. |
| 6,128,958 A | 10/2000 | Cain |
| 6,143,018 A | 11/2000 | Beuthan et al. |
| 6,165,144 A | 12/2000 | Talish et al. |
| 6,176,842 B1 | 1/2001 | Tachibana et al. |
| 6,308,585 B1 | 10/2001 | Nilsson et al. |
| 6,308,710 B1 | 10/2001 | Silva |
| 6,309,355 B1 | 10/2001 | Cain et al. |
| 6,318,146 B1 | 11/2001 | Madsen et al. |
| 6,321,109 B2 | 11/2001 | Ben-Haim et al. |
| 6,338,566 B1 | 1/2002 | Verdier |
| 6,344,489 B1 | 2/2002 | Spears |
| 6,391,020 B1 | 5/2002 | Kurtz et al. |
| 6,413,216 B1 | 7/2002 | Cain et al. |
| 6,419,648 B1 | 7/2002 | Vitek et al. |
| 6,470,204 B1 | 10/2002 | Uzgiris et al. |
| 6,488,639 B1 | 12/2002 | Ribault et al. |

(56) References Cited

U.S. PATENT DOCUMENTS

| | | |
|---|---|---|
| 6,490,469 B2 | 12/2002 | Candy |
| 6,500,141 B1 | 12/2002 | Irion et al. |
| 6,506,154 B1 | 1/2003 | Ezion et al. |
| 6,506,171 B1 | 1/2003 | Vitek et al. |
| 6,508,774 B1 | 1/2003 | Acker et al. |
| 6,511,428 B1 | 1/2003 | Azuma et al. |
| 6,511,444 B2 | 1/2003 | Hynynen et al. |
| 6,522,142 B1 | 2/2003 | Freundlich |
| 6,524,251 B2 | 2/2003 | Rabiner et al. |
| 6,536,553 B1 | 3/2003 | Scanlon |
| 6,543,272 B1 | 4/2003 | Vitek |
| 6,556,750 B2 | 4/2003 | Constantino et al. |
| 6,559,644 B2 | 5/2003 | Froundlich et al. |
| 6,576,220 B2 | 6/2003 | Unger |
| 6,599,288 B2 | 7/2003 | Maguire et al. |
| 6,607,498 B2 | 8/2003 | Eshel |
| 6,612,988 B2 | 9/2003 | Maor et al. |
| 6,613,004 B1 | 9/2003 | Vitek et al. |
| 6,613,005 B1 | 9/2003 | Friedman et al. |
| 6,626,854 B2 | 9/2003 | Friedman et al. |
| 6,626,855 B1 | 9/2003 | Weng et al. |
| 6,645,162 B2 | 11/2003 | Friedman et al. |
| 6,648,839 B2 | 11/2003 | Manna et al. |
| 6,666,833 B1 | 12/2003 | Friedman et al. |
| 6,685,640 B1 | 2/2004 | Fry et al. |
| 6,685,657 B2 | 2/2004 | Jones |
| 6,705,994 B2 | 3/2004 | Vortman et al. |
| 6,719,449 B1 | 4/2004 | Laugharn, Jr. et al. |
| 6,719,694 B2 | 4/2004 | Weng et al. |
| 6,735,461 B2 | 5/2004 | Vitek et al. |
| 6,736,814 B2 | 5/2004 | Manna et al. |
| 6,750,463 B1 | 6/2004 | Riley |
| 6,770,031 B2 | 8/2004 | Hynynen et al. |
| 6,775,438 B1 | 8/2004 | Gaedke et al. |
| 6,788,977 B2 | 9/2004 | Fenn et al. |
| 6,790,180 B2 | 9/2004 | Vitek |
| 6,820,160 B1 | 11/2004 | Allman |
| 6,852,082 B2 | 2/2005 | Strickberger et al. |
| 6,869,439 B2 | 3/2005 | White et al. |
| 6,890,332 B2 | 5/2005 | Truckai et al. |
| 6,929,609 B2 | 8/2005 | Asafusa |
| 7,004,282 B2 | 2/2006 | Manna et al. |
| 7,059,168 B2 | 6/2006 | Hibi et al. |
| 7,128,711 B2 | 10/2006 | Medan et al. |
| 7,128,719 B2 | 10/2006 | Rosenberg |
| 7,175,596 B2 | 2/2007 | Vitek et al. |
| 7,196,313 B2 | 3/2007 | Quinones |
| 7,223,239 B2 | 5/2007 | Schulze et al. |
| 7,258,674 B2 | 8/2007 | Cribbs et al. |
| 7,273,458 B2 | 9/2007 | Prausnitz et al. |
| 7,273,459 B2 | 9/2007 | Desilets et al. |
| 7,300,414 B1 | 11/2007 | Holland et al. |
| 7,311,679 B2 | 12/2007 | Desilets et al. |
| 7,331,951 B2 | 2/2008 | Eshel et al. |
| 7,341,569 B2 | 3/2008 | Soltani et al. |
| 7,347,855 B2 | 3/2008 | Eshel et al. |
| 7,358,226 B2 | 4/2008 | Dayton et al. |
| 7,359,640 B2 | 4/2008 | Onde et al. |
| 7,367,948 B2 | 5/2008 | O'Donnell et al. |
| 7,374,551 B2 | 5/2008 | Liang et al. |
| 7,377,900 B2 | 5/2008 | Vitek et al. |
| 7,442,168 B2 | 10/2008 | Novak et al. |
| 7,462,488 B2 | 12/2008 | Madsen et al. |
| 7,559,905 B2 | 7/2009 | Kagosaki et al. |
| 7,656,638 B2 | 2/2010 | Laakso et al. |
| 8,057,408 B2 * | 11/2011 | Cain ................ A61B 17/22004 601/2 |
| 8,333,115 B1 | 12/2012 | Garvey et al. |
| 8,539,813 B2 | 9/2013 | Cain et al. |
| 9,049,783 B2 | 6/2015 | Teofilovic |
| 9,061,131 B2 | 6/2015 | Jahnke et al. |
| 9,144,694 B2 | 9/2015 | Cain |
| 2001/0039420 A1 | 11/2001 | Burbank et al. |
| 2001/0041163 A1 | 11/2001 | Sugita |
| 2002/0045890 A1 | 4/2002 | Celliers et al. |
| 2002/0078964 A1 | 6/2002 | Kovac et al. |
| 2002/0099356 A1 | 7/2002 | Unger et al. |
| 2003/0092982 A1 | 5/2003 | Eppstein |
| 2003/0112922 A1 | 6/2003 | Burdette et al. |
| 2003/0149352 A1 | 8/2003 | Liang et al. |
| 2003/0157025 A1 | 8/2003 | Unger et al. |
| 2003/0181833 A1 | 9/2003 | Faragalla et al. |
| 2003/0199857 A1 | 10/2003 | Eizenhofer |
| 2003/0221561 A1 | 12/2003 | Milo |
| 2003/0236539 A1 | 12/2003 | Rabiner et al. |
| 2004/0127815 A1 | 7/2004 | Marchitto et al. |
| 2004/0138563 A1 | 7/2004 | Moehring et al. |
| 2004/0236248 A1 | 11/2004 | Svedman |
| 2004/0243021 A1 | 12/2004 | Murphy et al. |
| 2005/0038339 A1 | 2/2005 | Chauhan et al. |
| 2005/0038361 A1 | 2/2005 | Zhong et al. |
| 2005/0152561 A1 | 7/2005 | Spencer |
| 2005/0154314 A1 | 7/2005 | Quistgaard |
| 2005/0283098 A1 | 12/2005 | Conston et al. |
| 2006/0060991 A1 | 3/2006 | Holsteyns et al. |
| 2006/0074303 A1 | 4/2006 | Chornenky et al. |
| 2006/0173387 A1 | 8/2006 | Hansmann et al. |
| 2006/0206028 A1 | 9/2006 | Lee et al. |
| 2006/0241466 A1 | 10/2006 | Ottoboni et al. |
| 2006/0241523 A1 | 10/2006 | Sinelnikov et al. |
| 2006/0264760 A1 | 11/2006 | Liu et al. |
| 2006/0293630 A1 | 12/2006 | Manna et al. |
| 2007/0010805 A1 | 1/2007 | Fedewa et al. |
| 2007/0016039 A1 | 1/2007 | Vortman et al. |
| 2007/0044562 A1 | 3/2007 | Sarr |
| 2007/0065420 A1 | 3/2007 | Johnson |
| 2007/0083120 A1 | 4/2007 | Cain et al. |
| 2007/0161902 A1 | 7/2007 | Dan |
| 2007/0167764 A1 | 7/2007 | Hynynen |
| 2007/0205785 A1 | 9/2007 | Nilsson |
| 2007/0219448 A1 | 9/2007 | Seip et al. |
| 2008/0013593 A1 | 1/2008 | Kawabata |
| 2008/0055003 A1 | 3/2008 | Unnikrishnan et al. |
| 2008/0082026 A1 | 4/2008 | Schmidt et al. |
| 2008/0091125 A1 | 4/2008 | Owen et al. |
| 2008/0126665 A1 | 5/2008 | Burr et al. |
| 2008/0177180 A1 | 7/2008 | Azhari et al. |
| 2008/0194965 A1 | 8/2008 | Sliwa et al. |
| 2008/0214964 A1 | 9/2008 | Chapelon et al. |
| 2008/0262345 A1 | 10/2008 | Fichtinger et al. |
| 2008/0262486 A1 | 10/2008 | Zvuloni et al. |
| 2008/0312561 A1 | 12/2008 | Chauhan |
| 2008/0319376 A1 | 12/2008 | Wilcox et al. |
| 2009/0030339 A1 | 1/2009 | Cheng et al. |
| 2009/0112098 A1 | 4/2009 | Vaezy et al. |
| 2009/0177085 A1 | 7/2009 | Maxwell et al. |
| 2009/0198094 A1 | 8/2009 | Fenster et al. |
| 2009/0211587 A1 | 8/2009 | Lawrentschuk |
| 2009/0227874 A1 | 9/2009 | Suri et al. |
| 2009/0230822 A1 | 9/2009 | Kushculey et al. |
| 2010/0011845 A1 | 1/2010 | Laugharn et al. |
| 2010/0059264 A1 | 3/2010 | Hasegawa et al. |
| 2010/0069797 A1 | 3/2010 | Cain et al. |
| 2010/0125225 A1 | 5/2010 | Gelbart et al. |
| 2010/0152624 A1 | 6/2010 | Tanis et al. |
| 2010/0163694 A1 | 7/2010 | Fadler et al. |
| 2010/0261994 A1 | 10/2010 | Davalos et al. |
| 2010/0274136 A1 | 10/2010 | Cerofolini |
| 2010/0286519 A1 | 11/2010 | Lee et al. |
| 2010/0305432 A1 | 12/2010 | Duhay et al. |
| 2010/0317971 A1 | 12/2010 | Fan et al. |
| 2011/0054315 A1 | 3/2011 | Roberts et al. |
| 2011/0054363 A1 * | 3/2011 | Cain ................ A61B 17/225 601/4 |
| 2011/0067624 A1 * | 3/2011 | Cain ................ A61B 8/587 116/201 |
| 2011/0112400 A1 | 5/2011 | Emery et al. |
| 2011/0118602 A1 | 5/2011 | Weng et al. |
| 2011/0172529 A1 | 7/2011 | Gertner |
| 2011/0178444 A1 | 7/2011 | Slayton et al. |
| 2011/0251528 A1 | 10/2011 | Canney et al. |
| 2011/0257524 A1 | 10/2011 | Gertner |
| 2011/0263967 A1 | 10/2011 | Bailey et al. |
| 2012/0010541 A1 | 1/2012 | Cain et al. |

(56) References Cited

U.S. PATENT DOCUMENTS

| | | |
|---|---|---|
| 2012/0029353 A1 | 2/2012 | Slayton et al. |
| 2012/0059264 A1 | 3/2012 | Hope Simpson et al. |
| 2012/0059285 A1 | 3/2012 | Soltani et al. |
| 2012/0092724 A1 | 4/2012 | Pettis |
| 2012/0130288 A1 | 5/2012 | Holland et al. |
| 2012/0172720 A1 | 7/2012 | Kawabata |
| 2012/0189998 A1 | 7/2012 | Kruecker et al. |
| 2012/0232388 A1 | 9/2012 | Curra et al. |
| 2012/0259250 A1 | 10/2012 | Sapozhnikov et al. |
| 2012/0271167 A1 | 10/2012 | Holland et al. |
| 2012/0271223 A1 | 10/2012 | Khanna |
| 2013/0053691 A1 | 2/2013 | Kawabata et al. |
| 2013/0090579 A1 | 4/2013 | Cain et al. |
| 2013/0102932 A1 | 4/2013 | Cain et al. |
| 2013/0190623 A1 | 7/2013 | Bertolina et al. |
| 2013/0289593 A1 | 10/2013 | Hall et al. |
| 2013/0303906 A1 | 11/2013 | Cain et al. |
| 2014/0058293 A1 | 2/2014 | Hynynen et al. |
| 2014/0073995 A1 | 3/2014 | Teofilovic et al. |
| 2014/0100459 A1 | 4/2014 | Xu et al. |
| 2015/0011916 A1 | 1/2015 | Cannata et al. |
| 2015/0258352 A1 | 9/2015 | Lin et al. |
| 2015/0290477 A1 | 10/2015 | Jahnke et al. |
| 2016/0135916 A1 | 5/2016 | Rakic et al. |

FOREIGN PATENT DOCUMENTS

| | | |
|---|---|---|
| DE | 3544628 A1 | 6/1987 |
| DE | 3817094 A1 | 11/1989 |
| DE | 4012760 A1 | 5/1992 |
| EP | 0017382 A1 | 10/1980 |
| EP | 0320303 A2 | 6/1989 |
| EP | 0332871 A2 | 9/1989 |
| EP | 0384831 A2 | 8/1990 |
| EP | 0755653 A1 | 1/1997 |
| EP | 1374785 A1 | 1/2004 |
| EP | 1504713 A1 | 2/2005 |
| EP | 2397188 A1 | 12/2011 |
| GB | 2099582 A | 12/1982 |
| JP | 60-80779 A | 5/1985 |
| JP | 61-196718 A | 8/1986 |
| JP | HEI 2-215451 | 8/1990 |
| JP | HEI 6-197907 A | 7/1994 |
| JP | HEI 7-504339 A | 5/1995 |
| JP | 08-84740 A | 4/1996 |
| JP | 06-304178 A | 5/1996 |
| JP | 08-131454 A | 5/1996 |
| JP | 09-55571 A | 2/1997 |
| JP | HEI 10-512477 | 12/1998 |
| JP | 2000300559 A | 10/2000 |
| JP | 2003-510159 A | 3/2003 |
| JP | 2004-505660 A | 2/2004 |
| JP | 2005167058 A | 6/2005 |
| JP | 2007520307 A | 7/2007 |
| JP | 2010019554 A | 1/2010 |
| JP | 2010029650 A | 2/2010 |
| JP | 2010204068 A | 9/2010 |
| JP | 2004-512502 A | 4/2014 |
| WO | WO 94/06355 A1 | 3/1994 |
| WO | WO 02/32506 A1 | 4/2002 |
| WO | WO2005/018469 A1 | 3/2005 |
| WO | WO 2008/051484 A2 | 5/2008 |
| WO | WO2011/040054 A1 | 7/2011 |
| WO | WO 2011/092683 A1 | 8/2011 |
| WO | WO2011/154654 A2 | 12/2011 |

OTHER PUBLICATIONS

Maxwell et al.; In-vivo study of non-invasive thrombolysis by histotripsy in a porcine model; IEEE international Ultrasonics Symposium; IEEE; p. 220-223; Sep. 20, 2009.

Urban et al.; Measurement of prostate viscoelasticity using shearwave dispersion ultrasound vibrometry (SDUV): an in vitro study; IEEE International Ultrasonics Symposium Proceedings (IUS); pp. 1141-1144; Oct. 11, 2010.

Billson et al.; Rapid prototyping technologies for ultrasonic beam focussing in NDE; IEEE International Ultrasonic Symposium Proceedings; pp. 2472-2472; Oct. 2011.

Khokhlova et al.; Controlled tissue emulsification produced by high intensity focused ultrasound shock waves and millisecond boiling; J. Acoust. Soc. Am.; 130(5), pt. 2; pp. 3498-3510; Nov. 2011.

Cain et al.; U.S. Appl. No. 14/911,273 entitled "Histotripsy using very short ultrasound pulses," filed Feb. 10, 2016.

Hall et al.; U.S. Appl. No. 15/583,852 entitled "Method of manufacturing an ultrasound system," filed May 1, 2017.

Akiyama et al.; Elliptically curved acoustic lens for emitting strongly focused finite-amplitude beams: Application of the spheroidal beam equation model to the theoretical prediction; Acoustical Science and Technology, vol. 26, pp. 279-284, May 2005.

Appel et al.; Stereoscopic highspeed recording of bubble filaments; Ultrasonics Sonochemistry; vol. 11(1); pp. 39-42; Jan. 2004.

Aschoff et al.; How does alteration of hepatic blood flow affect liver perfusion and radiofrequency-induced thermal lesion size in rabbit liver?; J Magn Reson Imaging; 13(1); pp. 57-63; Jan. 2001.

Atchley et al.; Thresholds for cavitation produced in water by pulsed ultrasound; Ultrasonics.; vol. 26(5); pp. 280-285; Sep. 1988.

Avago Technologies; ACNV2601 High Insulation Voltage 10 MBd Digital Opotcoupler. Avago Technologies Data Sheet; pp. 1-11; Jul. 29, 2010.

Avago Technologies; Avago's ACNV2601 optocoupler is an optically coupled logic gate. Avago Technologies is a leading supplier of Solid State Relay (SSR), automotive digital isolator, logic interface optocoupler, and IPM interface optocoupler products; Data Sheet; 2 pages; Jul. 29, 2010.

Avtech; AVR-8 Data sheet; May 23, 2004; 3 pages; retrieved from the internet (http//www.avtechpulse.com).

Bjoerk et al.; Cool/MOS CP—How to make most beneficial use of the generation of super junction technology devices. Infineon Technologies AG. Feb. 2007 [retrieved Feb. 4, 2014] from the Internet (http://www.infineon.com/dgdl/Infineon+-+Application+Note+-+PowerMOSFETs+-+600V+CoolMOS%E284%A2+-+CP+Most+beneficial+use+of+superjunction+technologie+devices.pdf?folderId=db3a304412b407950112b408e8c90004&fileId=db3a304412b407950112b40ac9a40688>pages1 , 4, 14.

Bland et al.; Surgical Oncology; McGraw Hill; Chap. 5 (Cavitron Ultrasonic Aspirator); pp. 461-462; Jan. 29, 2001.

Burdin et al.; Implementation of the laser diffraction technique for cavitation bubble investigations; Particle & Particle Systems Characterization; vol. 19; pp. 73-83; May 2002.

Cain, Charles A.; Histotripsy: controlled mechanical sub-division of soft tissues by high intensity pulsed ultrasound (conference presentation); American Institute of Physics (AIP) Therapeutic Ultrasound: 5th International Symposium on Therapeutic Ultrasound; 44 pgs.; Oct. 27-29, 2005.

Canney et al.; Shock-Induced Heating and Millisecond Boiling in Gels and Tissue Due to High Intensity Focused Ultrasound; Ultrasound in Medicine & Biology, vol. 36, pp. 250-267; Feb. 2010 (author manuscript).

Chan et al.; An image-guided high intensity focused ultrasound device for uterine fibroids treatment; Medical Physics, vol. 29, pp. 2611-2620, Nov. 2002.

Clasen et al.; MR-guided radiofrequency ablation of hepatocellular carcinoma: Long-term effectiveness; J Vasc Interv Radiol; 22(6); pp. 762-770; Jun. 2011.

Clement et al.; A hemisphere array for non-invasive ultrasound brain therapy and surgery; Physics in Medicine and Biology, vol. 45, p. 3707-3719, Dec. 2000.

Cline et al.; Magnetic resonance-guided thermal surgery; Magnetic Resonance in Medicine; 30(1); pp. 98-106; Jul. 1993.

Curiel et al.; Elastography for the follow-up of high-intensity focused ultrasound prostate cancer treatment: Initial comparison with MRI; Ultrasound Med. Biol; 31(11); pp. 1461-1468; Nov. 2005.

Desilets et al.; The Design of Efficient Broad-Band Piezoelectric Transducers; Sonics and Ultrasonics, IEEE Transactions on, vol. 25, pp. 115-125, May 1978.

(56) References Cited

OTHER PUBLICATIONS

Emelianov et al.; Triplex ultrasound: Elasticity imaging to age deep venous thrombosis; Ultrasound Med Biol; 28(6); pp. 757-767; Jun. 2002.
Giannatsis et al.; Additive fabrication technologies applied to medicine and health care: a review; The International Journal of Advanced Manufacturing Technology; 40(1-2); pp. 116-127; Jan. 2009.
Gudra et al.; Influence of acoustic impedance of multilayer acoustic systems on the transfer function of ultrasonic airborne transducers; Ultrasonics, vol. 40, pp. 457-463, May 2002.
Hall et al.; A Low Cost Compact 512 Channel Therapeutic Ultrasound System For Transcutaneous Ultrasound Surgery; AIP Conference Proceedings, Boston, MA; vol. 829, pp. 445-449, Oct. 27-29, 2005.
Hall et al.; Acoustic Access to the Prostate for Extracorporeal Ultrasound Ablation; Journal of Endourology, vol. 24, pp. 1875-1881, Nov. 2010.
Hall et al.; Histotripsy of the prostate: dose effects in a chronic canine model; Urology; 74(4); pp. 932-937; Oct. 2009 (author manuscript).
Hall et al.; Imaging feedback of tissue liquefaction (histotripsy) in ultrasound surgery; IEEE Ultrasonic Symposium, Sep. 18-21, 2005, pp. 1732-1734.
Hartmann; Ultrasonic properties of poly(4-methyl pentene-1), Journal of Applied Physics, vol. 51, pp. 310-314, Jan. 1980.
Holland et al.; Thresholds for transient cavitation produced by pulsed ultrasound in a controlled nuclei environment; J. Acoust. Soc. Am.; vol. 88(5); pp. 2059-2069; Nov. 1990.
Huber et al.; Influence of shock wave pressure amplitude and pulse repetition frequency on the lifespan, size and number of transient cavities in the field of an electromagnetic lithotripter; Physics in Medicine and Biology; vol. 43(10); pp. 3113-3128; Oct. 1998.
Hynynen et al.; Tissue thermometry during ultrasound exposure; European Urology; 23(Suppl 1); pp. 12-16; 1993 (year of pub. sufficiently earlier than effective US filing date and any foreign priority date).
Kallel et al.; The feasibility of elastographic visualization of HIFU-induced thermal lesions in soft tissues: Image-guided high-intensity focused ultrasound; Ultrasound Med. Biol; 25(4); pp. 641-647; May 1999.
Kim et al.; Dependence of particle volume fraction on sound velocity and attenuation of EPDM composites; Ultrasonics, vol. 46, pp. 177-183, Feb. 2007.
Konofagou; Quo vadis elasticity imaging?; Ultrasonics; 42(1-9); pp. 331-336; Apr. 2004.
Krimholtz et al.; New equivalent circuits for elementary piezoelectric transducers; Electronics Letters, vol. 6, pp. 398-399, Jun. 1970.
Kruse et al.; Tissue characterization using magnetic resonance elastography: Preliminary results; Phys. Med. Biol; 45(6); pp. 1579-1590; Jun. 2000.
Lake et al.; Histotripsy: minimally invasive technology for prostatic tissue ablation in an in vivo canine model; Urology; 72(3); pp. 682-686; Sep. 2008.
Lauterborn et al.; Cavitation bubble dynamics studied by high speed photography and holography: part one; Ultrasonics; vol. 23; pp. 260-268; Nov. 1985.
Lensing et al.; Deep-vein thrombosis; The Lancet, vol. 353, pp. 479-485, Feb. 6, 1999.
Liu et al.; Real-time 2-D temperature imaging using ultrasound; IEEE Trans Biomed Eng; 57(1); pp. 12-16; Jan. 2010 (author manuscript, 16 pgs.).
Liu et al.; Viscoelastic property measurement in thin tissue constructs using ultrasound; IEEE Trans Ultrason Ferroelectr Freq Control; 55(2); pp. 368-383; Feb. 2008 (author manuscript, 37 pgs.).
Manes et al.; Design of a Simplified Delay System for Ultrasound Phased Array Imaging; Sonics and Ultrasonics, IEEE Transactions on, vol. 30, pp. 350-354, Nov. 1983.
Maréchal et al; Effect of Radial Displacement of Lens on Response of Focused Ultrasonic Transducer; Japanese Journal of Applied Physics, vol. 46, p. 3077-3085; May 15, 2007.
Maréchal et al; Lens-focused transducer modeling using an extended KLM model; Ultrasonics, vol. 46, pp. 155-167, May 2007.
Martin et al.; Water-cooled, high-intensity ultrasound surgical applicators with frequency tracking; Ultrasonics, Ferroelectrics and Frequency Control, IEEE Transactions on, vol. 50, pp. 1305-1317, Oct. 2003.
Maxwell et al.; Noninvasive Thrombolysis Using Pulsed Ultrasound Cavitation Therapy—Histotripsy; Ultrasound in Medicine & Biology, vol. 35, pp. 1982-1994, Dec. 2009 (author manuscript).
Maxwell; Noninvasive thrombolysis using histotripsy pulsed ultrasound cavitation therapy; PhD Dissertation. University of Michigan, Ann Arbor, Michigan. Jun. 2012.
Miller et al.; A review of in vitro bioeffects of inertial ultrasonic cavitation from a mechanistic perspective; Ultrasound in Medicine and Biology; vol. 22; pp. 1131-1154; (year of publication is sufficiently earlier than the effective U.S. filing date and any foreign priority date) 1996.
Nightingale et al.; Analysis of contrast in images generated with transient acoustic radiation force; Ultrasound Med Biol; 32(1); pp. 61-72; Jan. 2006.
Ohl et al.; Bubble dynamics, shock waves and sonoluminescence; Phil. Trans. R. Soc. Lond. A; vol. 357; pp. 269-294; (year of publication is sufficiently earlier than the effective U.S. filing date and any foreign priority date) 1999.
Okada et al.; A case of hepatocellular carcinoma treated by MR-guided focused ultrasound ablation with respiratory gating; Magn Reson Med Sci; 5(3); pp. 167-171; Oct. 2006.
Palmeri et al.; Acoustic radiation force-based elasticity imaging methods; Interface Focus; 1; pp. 553-564; Aug. 2011.
Parsons et al.; Cost-effective assembly of a basic fiber-optic hydrophone for measurement of high-amplitude therapeutic ultrasound fields; The Journal of the Acoustical Society of America, vol. 119, pp. 1432-1440, Mar. 2006.
Parsons et al.; Pulsed cavitational ultrasound therapy for controlled tissue homogenization; Ultrasound in Med. & Biol.; vol. 32(1); pp. 115-129; Jan. 2006.
Pishchalnikov et al.; Cavitation Bubble Cluster Activity in the Breakage of Kidney Stones by Lithotripter Shock Waves; J Endourol.; 17(7): 435-446; Sep. 2003.
Porter et al.; Reduction in left ventricular cavitary attenuation and improvement in posterior myocardial contrast . . . ; J Am Soc Echocardiography; pp. 437-441; Jul.-Aug. 1996.
Roberts et al.; Pulsed cavitational ultrasound: a noninvasive technology for controlled tissue ablation (histotripsy) in the rabbit kidney; Journal of Urology; vol. 175(2); pp. 734-738; Feb. 2006.
Rosenschein et al.; Ultrasound Imaging-Guided Noninvasive Ultrasound Thrombolysis: Preclinical Results; Circulation; vol. 102; pp. 238-245, Jul. 11, 2000.
Rowland et al.; MRI study of hepatic tumours following high intensity focused ultrasound surgery; British Journal of Radiology; 70; pp. 144-153; Feb. 1997.
Roy et al.; A precise technique for the measurement of acoustic cavitation thresholds and some preliminary results; Journal of the Acoustical Society of America; vol. 78(5); pp. 1799-1805; Nov. 1985.
Sapareto et al.; Thermal dose determination in cancer therapy; Int J Radiat Oncol Biol Phys; 10(6); pp. 787-800; Apr. 1984.
Sapozhnikov et al.; Ultrasound-Guided Localized Detection of Cavitation During Lithotripsy in Pig Kidney in Vivo; IEEE Ultrasonics Symposium, vol. 2; pp. 1347-1350; Oct. 7-10, 2001.
Sato et al.; Experimental Investigation of Phased Array Using Tapered Matching Layers. 2002 IEEE Ultrasound Symposium. vol. 2; pp. 1235-1238, Oct. 2002.
Simonin et al.; Characterization of heterogeneous structure in a polymer object manufactured by stereolithography with low-frequency microechography; Journal of Materials Chemistry; vol. 6, pp. 1595-1599, Sep. 1996.
Sokolov et al.; Use of a dual-pulse lithotripter to generate a localized and intensified cavitation field; Journal of the Acoustical Society of America; vol. 110(3); pp. 1685-1695; Sep. 2001.
Song et al.; Feasibility of Using Lateral Mode Coupling Method for a Large Scale Ultrasound Phased Array for Noninvasive Transcranial

(56) References Cited

OTHER PUBLICATIONS

Therapy; Biomedical Engineering; IEEE Transactions on, vol. 57, pp. 124-133; Jan. 2010 (author manuscript).
Souchon et al.; Visualisation of HIFU lesions using elastography of the human prostate in vivo: Preliminary results; Ultrasound Med. Biol; 29(7); pp. 1007-1015; Jul. 2003.
Souquet et al.; Design of Low-Loss Wide-Band Ultrasonic Transducers for Noninvasive Medical Application; Sonics and Ultrasonics, IEEE Transactions on, vol. 26, pp. 75-80, Mar. 1979.
Therapeutic Ultrasound Group. Non-invasive Ultrasonic Tissue Fraction for Treatment of Benign Disease and Cancer—"Histotripsy". University research [online]. Biomedical Engineering Department, University of Michigan. Jul. 2011[retrieved on Jan. 28, 2014] from: (http://web.archive.org/web/20110720091822/http://www.histotripsy.umich.edu/index.html>,entiredocument).
Toda; Narrowband impedance matching layer for high efficiency thickness mode ultrasonic transducers; Ultrasonics, Ferroelectrics and Frequency Control, IEEE Transactions on, vol. 49, pp. 299-306, Mar. 2002.
Van Kervel et al.; A calculation scheme for the optimum design of ultrasonic transducers; Ultrasonics, vol. 21, pp. 134-140, May 1983.
Wang et al.; Quantitative ultrasound backscatter for pulsed cavitational ultrasound therapy-histotripsy; Ultrasonics, Ferroelectrics and Frequency Control, IEEE Transactions on, vol. 56, pp. 995-1005, May 2009 (author manuscript).
Xie et al.; Correspondence of ultrasound elasticity imaging to direct mechanical measurement in aging DVT in rats; Ultrasound Med Biol; 31(10); pp. 1351-1359; Oct. 2005 (author manuscript, 20 pgs.).
Xu et al.; A new strategy to enhance cavitational tissue erosion by using a high intensity initiating sequence; IEEE Trans Ultrasonics Ferroelectrics and Freq Control; vol. 53(8); pp. 1412-1424; Aug. 2006.
Xu et al.; Controlled ultrasound tissue erosion: the role of dynamic interaction between insonation and microbubble activity; Journal of the Acoustical Society of America; vol. 117(1); pp. 424-435; Jan. 2005.
Xu et al.; Controlled ultrasound tissue erosion; IEEE Transaction on Ultrasonics, Ferroelectrics, and Frequency Control; vol. 51 (6); pp. 726-736; Jun. 2004.
Xu et al.; Effects of acoustic parameters on bubble cloud dynamics in ultrasound tissue erosion (histotripsy); Journal of the Acoustical Society of America; vol. 122(1); pp. 229-236; Jul. 2007.
Xu et al.; High Speed Imaging of Bubble Clouds Generated in Pulsed Ultrasound Cavitational Therapy'Histotripsy; IEEE Trans Ultrason Ferroelectr Freq Control; ; vol. 54; No. 10; pp. 2091R2101; Oct. 2007.
Xu et al.; Investigation of intensity threshold for ultrasound tissue erosion; Ultrasound in Med. & Biol.; vol. 31(12); pp. 1673-1682; Dec. 2005.
Xu et al.; Optical and acoustic monitoring of bubble cloud dynamics at a tissue-fluid interface in ultrasound tissue erosion; Journal of the Acoustical Society of America; vol. 121(4); pp. 2421-2430; Apr. 2007.
Yan et al.; A review of rapid prototyping technologies and systems; Computer-Aided Design, vol. 28, pp. 307-318, Apr. 1996.
Zhang et al.; A fast tissue stiffness-dependent elastography for HIFU-induced lesions inspection; Ultrasonics; 51(8); pp. 857-869; Dec. 2011.
Zheng et al.; An acoustic backscatter-based method for localization of lesions induced by high-intensity focused ultrasound; Ultrasound Med Biol; 36(4); pp. 610-622; Apr. 2010.
Kim et al.; Lesion generation through ribs using histotripsy therapy without aberration correction; IEEE Trans Ultrason Ferroelectr Freq Control; 58(11):2334-43; Nov. 2011.
Kim et al.; Lesion Generation through Ribs without Aberration Correction using Cavitational Therapy; Ultrasonics Symposium (IUS), 2010 IEEE, pp. 346-349; Oct. 11-14, 2010.
Wu et al.; Extracorporeal high intensity focused ultrasound ablation in the treatment of 1038 patients with solid carcinomas in China: an overview; Ultrason Sonochem; 11(3):149-54; May 2004.
Arani et al.; Transurethral prostate magnetic resonance elestography; prospective imaging requirements; Magn. Reson. Med.; 65(2); pp. 340-349; Feb. 2011.
Maxwell et al.; Cavitation clouds created by shock scattering from bubbles during histotripsy; J. Acoust. Soc. Am.; 130(4); pp. 1888-1898; Oct. 2011.
Aubry et al.; Transcostal high-intensity-focused ultrasound: ex vivo adaptive focusing feasibility study; Phys Med Biol; 53(11):2937-51; Jun. 2008.
Ballard et al.; Adaptive transthoracic refocusing of dual-mode ultrasound arrays; IEEE Trans Biomed Eng; 57(1):93-102; Jan. 2010.
Bobkova et al.; Focusing of high-intensity ultrasound through the rib cage using a therapeutic random phased array; Ultrasound Med Biol; 36(6):888-906; Jun. 2010.
Botros et al.; Two-step hybrid virtual array ray (VAR) technique for focusing through the rib cage; Ultrasonics, Ferroelectrics and Frequency Control, IEEE Transactions on; 45(4):989-1000; Jul. 1998.
Civale et al.; The use of a segmented transducer for rib sparing in HIFU treatments; Ultrasound Med Biol; 32(11):1753-61; Nov. 2006.
Cochrad et al.; Ultrasonic focusing through the ribs using the DORT method; Med Phys; 36(8):3495-503; Aug. 2009.
Jung et al.; High-intensity focused ultrasound ablation in hepatic and pancreatic cancer: complications; Abdom Imaging; 36(2):185-95; Apr. 2011.
Kennedy et al.; High-intensity focused ultrasound for the treatment of liver tumours; Ultrasonics; vol. 42; No. 1-9; pp. 931-935; Apr. 2004.
Li et al.; Complications of high intensity focused ultrasound in patients with recurrent and metastatic abdominal tumors; World J Gastroenterol; 13(19):2747-51; May 2007.
Liu et al.; Focal beam distortion and treatment planning for transrib focused ultrasound thermal therapy: a feasibility study using a two-dimensional ultrasound phased array; Med Phys; 37(2):848-60; Feb. 2010.
Quesson et al.; A method for MRI guidance of intercostal high intensity focused ultrasound ablation in the liver; Med Phys; 37(6):2533-40; Jun. 2010.
Xu et al.; U.S. Appl. No. 15/713,441 entitled "Bubble-induced color doppler feedback during histotripsy," filed Sep. 22, 2017.
Xu et al.; U.S. Appl. No. 15/737,761 entitled "Histotripsy therapy systems and methods for the treatment of brain tissue," filed Dec. 19, 2017.
Wikipedia; Medical ultrasound; 15 pages; retrieved from the internet (https://en.wikipedia.org/w/index.php?title=Medical_utrasound&oldid=515340960) on Jan. 12, 2018.

* cited by examiner

LESION GENERATION THROUGH BONE USING HISTOTRIPSY THERAPY WITHOUT ABERRATION CORRECTION

CROSS REFERENCE TO RELATED APPLICATIONS

This application is a continuation of U.S. patent application Ser. No. 13/570,708, filed Aug. 9, 2012, now U.S. Pat. No. 9,144,694, which application claims the benefit under 35U.S.C. 119 of U.S. Provisional Patent Application No. 61/521,986, filed Aug. 10, 2011, titled "Lesion Generation Through Bone Using Histotripsy Therapy Without Aberration Correction". These applications are herein incorporated by reference in their entirety.

GOVERNMENT INTEREST

This invention was made with government support under CA134579 awarded by the National Institutes of Health. The government has certain rights in the invention.

INCORPORATION BY REFERENCE

All publications and patent applications mentioned in this specification are herein incorporated by reference to the same extent as if each individual publication or patent application was specifically and individually indicated to be incorporated by reference.

FIELD

The present disclosure generally relates to providing therapy to tissue with ultrasound energy. More specifically, the present disclosure describes damaging tissue with Histotripsy therapy in the presence of intervening tissue or bones.

BACKGROUND

The effects of acoustic obstruction from rib and other bones have long been a challenge to researchers in high intensity focused ultrasound (HIFU). In several non-invasive surgery applications, such as treatment for liver and pancreatic cancer, it is often the case that the available acoustic windows are partially blocked by the ribs, which can substantially decrease the ultrasound energy delivery to the focal target and may overheat overlying tissues due to the highly absorptive nature of bones. Furthermore, ribs can cause significant field aberration by introducing secondary lobes in the focal profile which can result in undesired collateral damage.

To overcome these issues, significant efforts have been dedicated to develop aberration correction algorithms in order to spare the ribs and improve beam forming. Theoretical studies on the application of virtual phased arrays to sonicate between the rib bones have been conducted; a physically segmented transducer design was also proposed to prevent sonication to the ribs by aligning active elements with the intercostal gaps. More recently, adaptive focal optimization algorithms for transcostal therapy have been developed, depending on the presence of a point source or an identifiable acoustic spot at the desired focus. More sophisticated non-invasive approaches using ultrasound scanning and time-reversal to identify the ribs require transducers with transmit and receive capabilities. Other non-invasive methods explored involve the use of CT or MRI to image the rib obstructions and selectively deactivate elements shadowed by the rib bones.

A major challenge facing trans-thoracic ablation using ultrasound is to overcome the rib obstruction. For example, skin burns and subcostal edema have been reported in clinical HIFU liver ablation cases. For transthoracic ablation of the liver using HIFU, ribs in the ultrasound pathway cause periodic blockage of ultrasound, resulting in a significantly decreased main lobe and increased grating lobes. Moreover, due to the high ultrasound absorption coefficient of bone and reflection effects at the bone-tissue interface, overheating of ribs and surrounding tissue often results in unwanted tissue damage. Phased arrays and aberration correction algorithms have been developed to switch off the elements blocked by the ribs to reduce overheating to the ribs and associated tissue. Even with these improvements, grating lobes may still remain producing undesired heating and collateral damage.

Similarly to trans-thoracic ultrasound ablation, transcranial ultrasound therapy is also very challenging, as the highly aberrating and attenuating effects introduced by the skull can severely distort the therapeutic focus and limit the effectiveness of the treatment. To counter those issues, HIFU systems use non-invasive CT or MR imaging technology to correct for the acoustic aberration effects from the skull (refs) or other sophisticated correction algorithms such as combination of time-reversal method and bubble signature (ref). One of the main challenges in thermal HIFU for transcranial therapy is the need to avoid undesired skull overheating effects, which limit the amount of ultrasound power that can be applied through the skull, even when active cooling is performed on the scalp, potentially reducing the effectiveness of the treatment.

The use of aberration correction algorithms has made it possible to perform noninvasive ultrasound therapy through bone obstruction. However, the difficulties in implementing these correction algorithms is the need for phased arrays and the added complexity of the associated electronics, imaging equipment, and computation. Furthermore, when bone obstacles are involved, secondary lobes may still be present in the focal profile even after correction algorithms are applied due to the periodic ultrasound blockage pattern caused by the bones. Even though a lesion may be generated without overheating the overlying bones using the correction algorithms, the treatment precision could still be poor due to the collateral damage resulted from the increased secondary lobes.

SUMMARY

In some embodiments, a method of treating tissue with ultrasound energy comprises positioning a focus of a histotripsy transducer on a target tissue, delivering histotripsy energy from the histotripsy transducer through a bone aberrator, forming a histotripsy bubble cloud on the focus, and preventing the formation of secondary histotripsy bubble clouds without implementing an aberration correction algorithm.

In some embodiments, the method further comprises imaging the focus with an ultrasound imaging system.

In another embodiment, the method further comprises, in the event that a secondary histotripsy bubble cloud develops away from the focus, decreasing a power level of the histotripsy transducer until the secondary bubble cloud disappears.

In one embodiment, the method further comprises damaging the target tissue at the focus.

In some embodiments, the delivering histotripsy energy step comprises delivering short (<20 μsec), high pressure (peak negative pressure >10 MPa) shockwave ultrasound pulses at a duty cycle <5%.

In one embodiment, the bone aberrator comprises a rib cage. In other embodiments, the bone aberrator comprises a skull or a pelvic bone.

In one embodiment, the method further comprises adjusting a position of the focus to a different portion of the target tissue, delivering histotripsy energy from the histotripsy transducer through the bone aberrator, and forming a histotripsy bubble cloud on the focus at the different portion of the target tissue.

In another embodiment, a method of treating tissue with ultrasound energy comprises positioning a focus of a histotripsy transducer on a target tissue, delivering histotripsy energy from the histotripsy transducer through a bone aberrator, and increasing a power level of the histotripsy transducer until a histotripsy bubble cloud develops at the focus.

In some embodiments, the increasing step further comprises increasing the power level of the histotripsy transducer until a histotripsy bubble cloud is imaged at the focus.

In another embodiment, the method comprises, in the event that a secondary histotripsy bubble cloud develops away from the focus, decreasing a power level of the histotripsy transducer until the secondary bubble cloud disappears.

In some embodiments, the method further comprises imaging the focus with an ultrasound imaging system.

In one embodiment, the method further comprises damaging the target tissue at the focus.

In some embodiments, the delivering histotripsy energy step comprises delivering short (<20 μsec), high pressure (peak negative pressure >10 MPa) shockwave ultrasound pulses at a duty cycle <5%.

In one embodiment, the bone aberrator comprises a rib cage. In other embodiments, the bone aberrator comprises a skull or a pelvic bone.

In one embodiment, the method further comprises adjusting a position of the focus to a different portion of the target tissue, delivering histotripsy energy from the histotripsy transducer through the bone aberrator, and forming a histotripsy bubble cloud on the focus at the different portion of the target tissue.

In yet another embodiment, a method of treating tissue with ultrasound energy is provided, comprising positioning a focus of a histotripsy transducer on a target tissue, delivering histotripsy energy from the histotripsy transducer through a bone aberrator, forming a histotripsy bubble cloud on the focus, observing formation of a secondary histotripsy bubble cloud positioned away from the focus, and decreasing a power level of the histotripsy transducer to eliminate the secondary histotripsy bubble cloud.

In some embodiments, the method further comprises imaging the focus with an ultrasound imaging system.

In one embodiment, the method further comprises damaging the target tissue at the focus.

In some embodiments, the delivering histotripsy energy step comprises delivering short (<20 μsec), high pressure (peak negative pressure >10 MPa) shockwave ultrasound pulses at a duty cycle <5%.

In one embodiment, the bone aberrator comprises a rib cage. In other embodiments, the bone aberrator comprises a skull or a pelvic bone.

In one embodiment, the method further comprises adjusting a position of the focus to a different portion of the target tissue, delivering histotripsy energy from the histotripsy transducer through the bone aberrator, and forming a histotripsy bubble cloud on the focus at the different portion of the target tissue.

In another embodiment, a method of treating tissue with ultrasound energy is provided, comprising delivering histotripsy energy from the histotripsy transducer through a bone aberrator, forming a histotripsy bubble cloud on a focus of the histotripsy transducer, forming a secondary histotripsy bubble cloud away from the focus of the histotripsy transducer, and decreasing a power level of the histotripsy transducer to eliminate the secondary histotripsy bubble cloud.

In some embodiments, the method further comprises imaging the focus with an ultrasound imaging system.

In one embodiment, the method further comprises damaging the target tissue at the focus.

In some embodiments, the delivering histotripsy energy step comprises delivering short (<20 μsec), high pressure (peak negative pressure >10 MPa) shockwave ultrasound pulses at a duty cycle <5%.

In one embodiment, the bone aberrator comprises a rib cage. In other embodiments, the bone aberrator comprises a skull or a pelvic bone.

In one embodiment, the method the method further comprises adjusting a position of the focus to a different portion of the target tissue, delivering histotripsy energy from the histotripsy transducer through the bone aberrator, and forming a histotripsy bubble cloud on the focus at the different portion of the target tissue.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

DETAILED DESCRIPTION

This disclosure describes using a specific form of pulsed therapeutic ultrasound, or Histotripsy, to non-invasively generate lesions through ribs or other intervening bone structures. Histotripsy therapy mechanically ablates tissue through the initiation and maintenance of a cavitation bubble cloud, which occurs when the focal pressure is above a certain threshold. Histotripsy can be configured to generate precise lesions through the ribs without aberration correction, as long as the main beam retains its shape and is above the cavitation cloud initiation threshold while secondary lobes are below the threshold.

In some embodiments, spherically focused transducers are used to generate lesions in tissue or tissue-mimicking phantoms with bone aberrators placed between the transducer and its focus. A high-speed camera or ultrasound imaging can be used to observe bubble cloud formation and lesion development in the tissue. Despite the high secondary lobes introduced by the bone aberrators, the therapy can be controlled so that single histotripsy bubble clouds of similar shape develop exclusively at the focus, resulting in well confined focal lesions with comparable dimensions. Collateral damage due to secondary lobes can therefore be limited and may comprise only marginal damage spots caused by single bubbles that fail to form a bubble cloud. Histotripsy therapy has a relatively high tolerance against aberrated fields and can generate confined focal lesions through rib obstacles without aberration correction.

This disclosure describes the use of Histotripsy therapy to generate lesions through rib or bone aberrators without applying any correction mechanisms other than transducer power modulation to compensate for attenuation effects. Histotripsy uses controlled cavitation bubble clouds to induce mechanical tissue fractionation. Histotripsy bubble clouds can be produced by delivering Histotripsy energy to tissue with a Histotripsy transducer, defined by using short (<20 μsec), high pressure (peak negative pressure >10 MPa) shockwave ultrasound pulses at a low duty cycle, typically <5%, minimizing thermal effects. Based on the high echogenicity of cavitating bubble clouds, treatment can also be readily monitored in real time using any conventional ultrasound imaging system, allowing the operator to acknowledge whether cavitation bubble clouds have been generated.

The tissue fractionation effect from Histotripsy therapy occurs when the focal pressure exceeds a certain threshold level at which a cavitation bubble cloud is initiated. Based on this threshold mechanism, Histotripsy therapy can be controlled to generate precise lesions through the ribs or bone provided that the pressure main beam maintains its shape and is above the bubble cloud initiation threshold while secondary lobes resulting from the bone aberrator remain below the threshold and thus do not initiate a cavitation bubble cloud.

Figure 1:
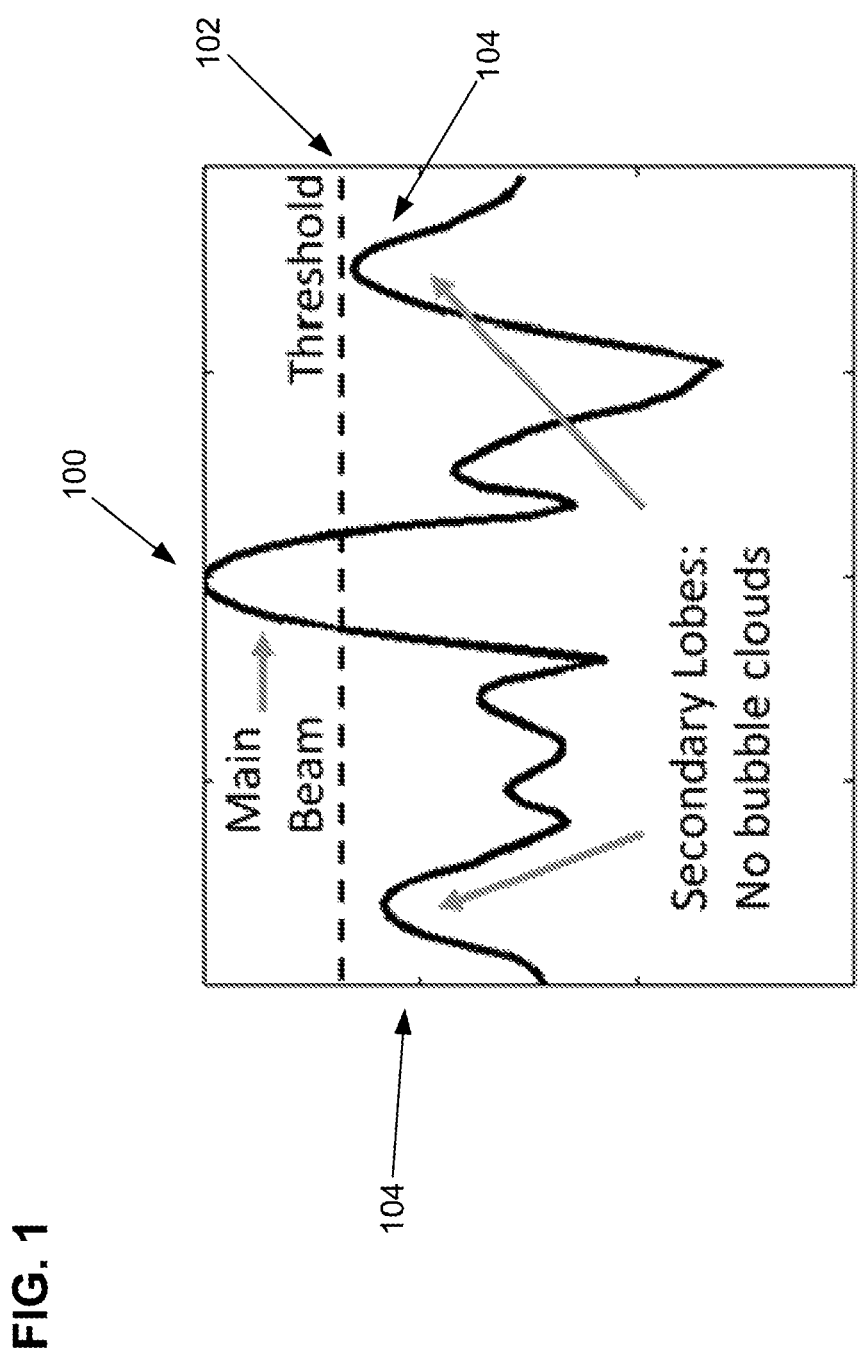
FIG. 1 is an illustration of the cavitation threshold effect in histotripsy therapy: By modulating the acoustic power in such a way that only the main beam is above the bubble cloud initiation threshold, confined focal lesions with minimal collateral damage should be generated at the treatment focus.

FIG. 1 illustrates a pressure main beam 100 of a Histotripsy therapy waveform above a bubble cloud initiation threshold 102 and therefore forming a cavitation bubble cloud, and secondary lobes 104 of the waveform below the threshold and therefore not forming a cavitation bubble cloud. Since no bubble clouds are generated in regions that are below the initiation threshold, with this approach there can be minimal collateral damage to regions surrounding the main lesion.

Figure 2:
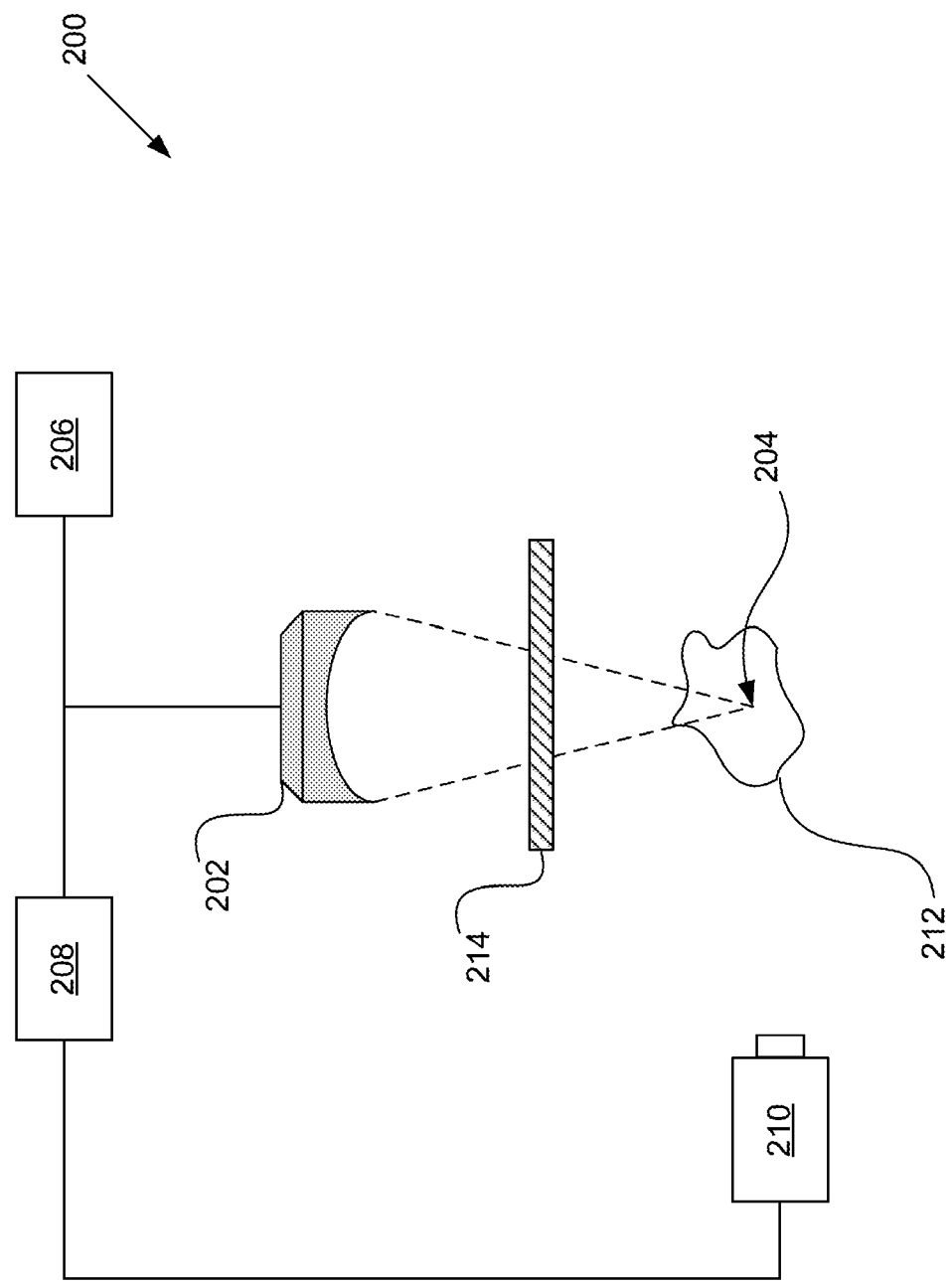
FIG. 2 is an illustration of the experimental setup for bubble cloud imaging.

FIG. 2 illustrates a Histotripsy system 200 configured to provide Histotripsy therapy to tissue. The system 200 can include a Histotripsy transducer 202 having a focus 204, a RF generator 206, controller 208, and imaging system 210. Also shown in FIG. 2 are a target tissue 212 and a bone aberrator 214. The system can be used in the presence of a bone aberrator (e.g., a rib) or absent a bone aberrator.

The histotripsy transducer 202 can comprise any transducer capable of producing histotripsy bubble clouds. More specifically, the transducer can be configured to produce a histotripsy bubble cloud by delivering ultrasonic energy using short (<20 μsec), high pressure (peak negative pressure >10 MPa) shockwave ultrasound pulses at a low duty cycle, typically <5%, minimizing thermal effects. In one embodiment, the transducer comprises a 750 kHz, 18 channel spherically focused transducer. The transducer can be positioned on or near the patient and coupled to the patient with an acoustic coupling medium, such as degassed water.

Generator 206 is configured to deliver the ultrasound pulses to transducer 202 via controller 208. Imaging system 210 is configured to monitor the histotripsy therapy from transducer 202, and can comprise any medical imaging system, preferably B-mode ultrasound imaging, a high speed camera, or a combination of the two. Bone aberrator 214 can comprise any bone found in the human body and positioned between the transducer and the target tissue 212, such as a rib, skull, or pelvic bone. The target tissue can comprise, for example, the heart, the liver, the brain, the pancreas, the prostate, or any other tissue or organ positioned under bone.

Lesions in the target tissue can be created through the bone aberrators by driving the transducer 202 with the RF generator 206 and controller 208 in such a way that the peak rarefactional pressure at the focus 204 was equivalent to that applied in treatments without an intervening bone aberrator. In some embodiments, treatment pulses can be applied at a pulse repetition frequency (PRF) of 100 Hz and 5 cycles per pulse.

The cavitation threshold and main beam vs. secondary lobes technique can be applied during Histotripsy therapy to ensure only the formation of a cavitational bubble cloud at a focal point of the Histotripsy transducer, such as the transducer and Histotripsy system described above in FIG. 2.

Referring to FIGS. 1 and 2, in one embodiment, tissue 212 can be treated with Histotripsy transducer 202 by first positioning focus 204 of the transducer on the target tissue 212, delivering Histotripsy energy from the transducer through bone aberrator 214 into the tissue, forming a Histotripsy cavitational bubble cloud on the tissue at the focus, and preventing formation of secondary histotripsy bubble clouds without implementing an aberration correction algorithm.

In another embodiment, tissue 212 can be treated with Histotripsy transducer 202 by first positioning focus 204 of the transducer on the target tissue 212, delivering Histotripsy energy from the transducer through bone aberrator 214 into the tissue, and increasing a power level of the histotripsy transducer until a histotripsy cavitational bubble cloud develops at the focus on the tissue.

In yet another embodiment, tissue 212 can be treated with Histotripsy transducer 202 by first positioning focus 204 of the transducer on the target tissue 212, delivering Histotripsy energy from the transducer through bone aberrator 214 into the tissue, forming a Histotripsy cavitational bubble cloud at the focus on the tissue, observing formation of at least one secondary Histotripsy cavitational bubble cloud positioned away from the focus, and decreasing a power level of the Histotripsy transducer to eliminate the at least one secondary Histotripsy cavitational bubble cloud.

In yet another embodiment, tissue 212 can be treated with Histotripsy transducer 202 by first positioning focus 204 of the transducer on the target tissue 212, delivering Histotripsy energy from the transducer through bone aberrator 214 into the tissue, forming a Histotripsy cavitational bubble cloud at the focus on the tissue, forming at least one secondary Histotripsy cavitational bubble cloud positioned away from the focus, and decreasing a power level of the Histotripsy transducer to eliminate the at least one secondary Histotripsy cavitational bubble cloud.

Histotripsy therapy is more resistant to the grating lobes caused by rib or other bone aberration, as the cavitation cloud is only generated when the pressure exceeds a distinct threshold. By using an appropriate pressure where the main lobe is above the threshold while the grating lobes are not, a confined cloud within the main lobe and a precise lesion can be produced despite the intervening ribs. Thermal damage to the overlying and surrounding tissue can be prevented by using a prolonged cooling time between pulses.

Figure 3:
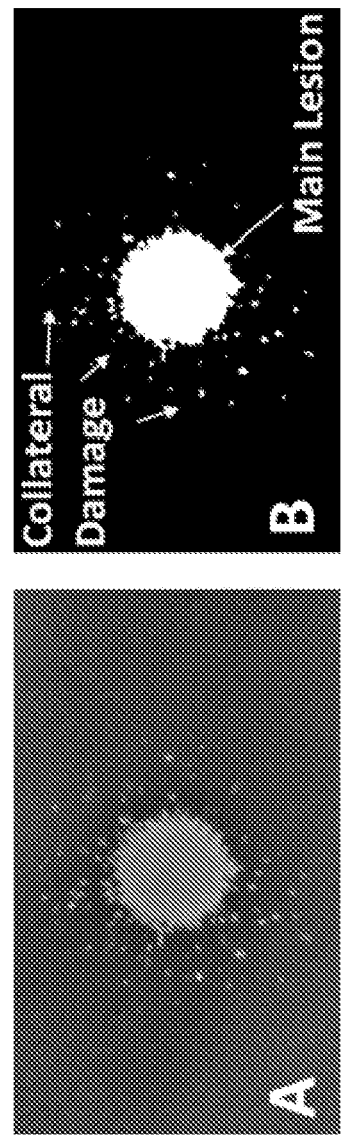
FIG. 3 illustrates (A) Sample picture of a treated RBC phantom showing a translucent lesion. (B) Processed image sample for lesion size and collateral damage assessment. Collateral damage appears as small damage spots surrounding the main lesion area.

Lesion sizes and collateral damage distribution can be assessed with the aid of an image analysis script which allows image binarization into fractionated and intact areas, with fractionated areas defined as zones with pixel intensities three standard deviations higher than the chosen background, typically the space-averaged intensity of pixels from a sample area on the intact blood layer. Once the image is binarized, lesion dimensions are then estimated by a pixel count. FIG. 3 illustrates (A) Sample picture of a treated tissue showing a translucent lesion. (B) Processed image sample for lesion size and collateral damage assessment. Collateral damage appears as small damage spots surrounding the main lesion area.

Without applying power compensation, the presence of bone aberrators can substantially reduce the peak rarefactional pressure amplitude at the focus. Pressure insertion losses can vary depending on the type of aberrators.

Figure 4:
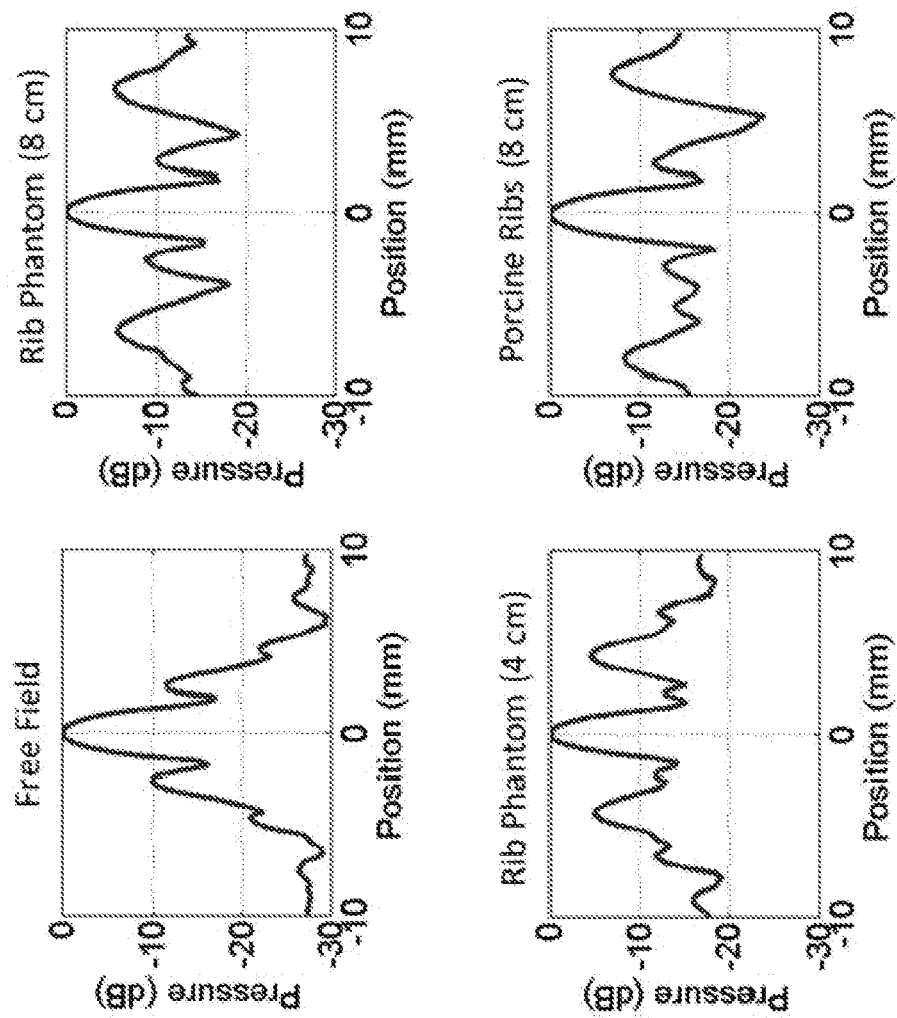
FIG. 4 shows normalized transversal focal pressure profiles obtained in free field and through the rib aberrators. Secondary lobes were not observed to develop in the longitudinal axis or the transversal axis parallel to the orientation of the rib obstacles. "Rib Phantom (8 cm)" indicates the rib phantom was placed between the transducer and the focus, 8 cm away from the focus.

In one experiment, high levels of secondary (grating) lobes were introduced in the focal profile along the transversal axis perpendicular to the orientation of the rib aberrators. No significant secondary lobe development was observed in the transversal axis parallel to the orientation of the obstacles or along the longitudinal axis of propagation. The highest secondary lobes were in the range of −7 dB to −4 dB normalized to their respective main lobes; −7 dB with porcine ribs and −4 dB with the rib phantom positioned at 4 cm from the focus (See FIG. 4). The location of the secondary lobes varied from 5-8 mm with respect to the center of the main beam, developing closer to the center when the rib obstacles were placed farther away from the transducer (closer to the focus).

Figure 5:
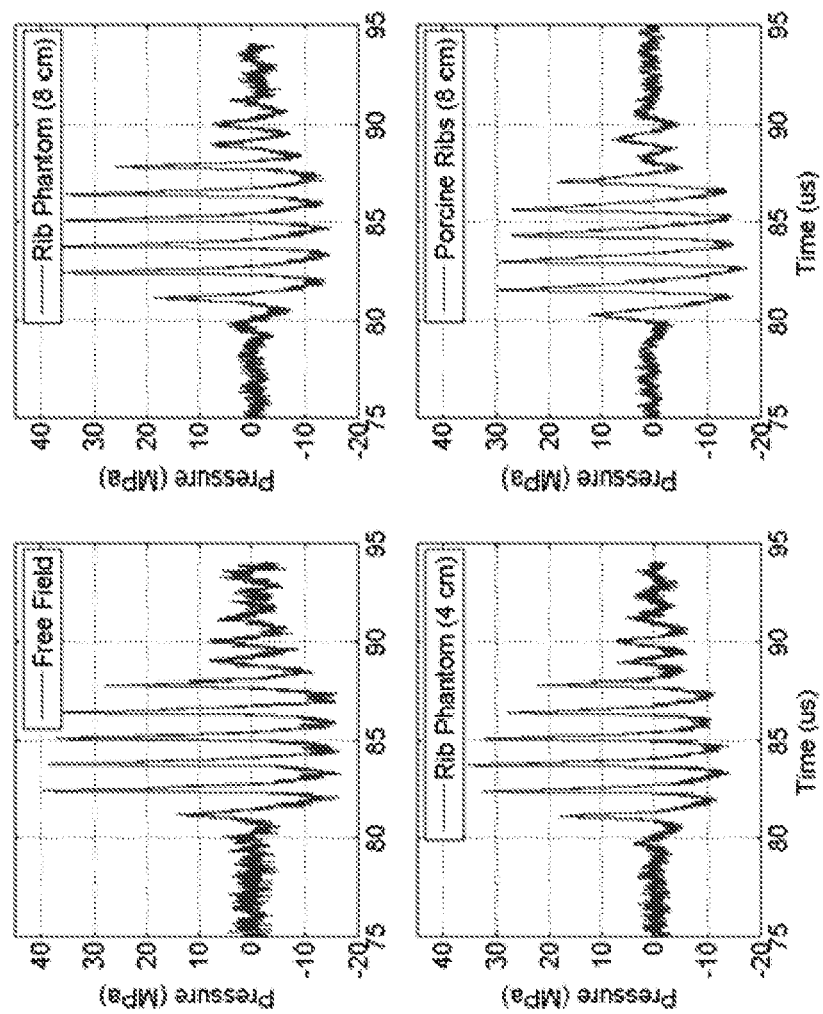
FIG. 5 illustrates treatment pulse waveforms measured in free field and through the rib aberrators.

In practice, the main beam does not undergo any noticeable shift in the transversal or longitudinal coordinates in the presence of a rib aberrator in the field. Despite the presence of high secondary lobes, the main beam can remain relatively undistorted in all cases. Because of the significant insertion losses measured in the presence of the bone aberrators, the transducer power can be appropriately increased to compensate for the attenuation and approximately equalize peak rarefactional pressure levels at the focus. In some embodiments, the peak rarefactional pressure levels at the focus can be within the range of 13-15 MPa (See FIG. 5).

Figure 6:
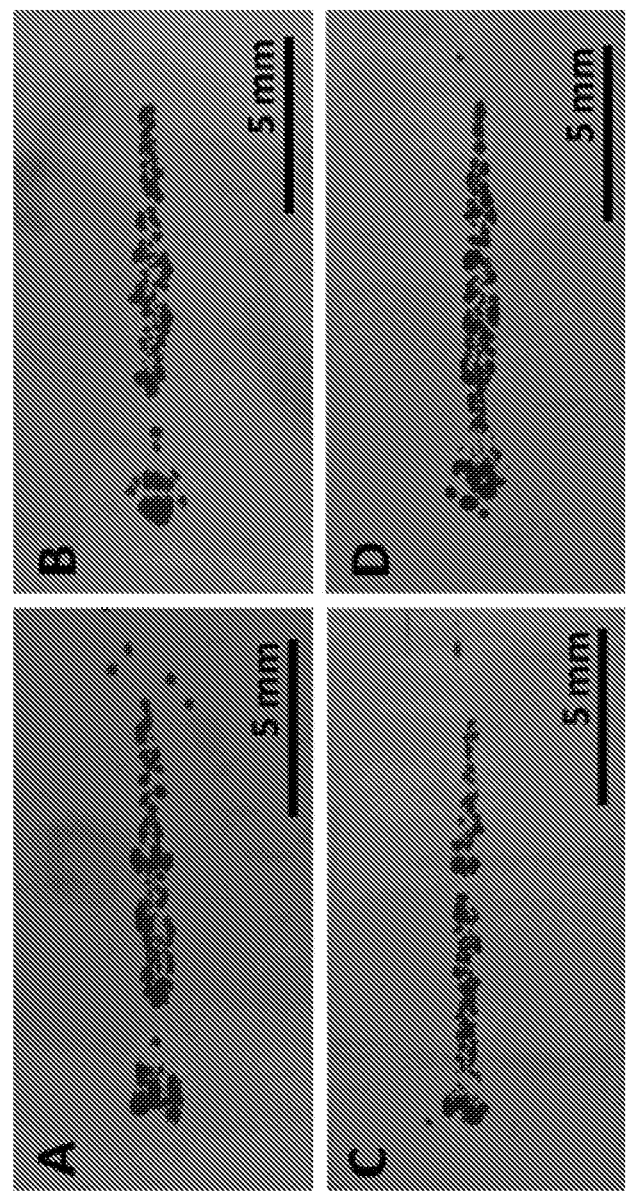
FIG. 6 shows high-speed images of bubble clouds (shown as the dark clusters of dots) generated in a transparent agarose phantom. (A) In free field; (B) with the rib phantom at 8 cm; (C) with the rib phantom at 4 cm; (D) with the porcine ribs at 8 cm. Longitudinal planes are shown. Ultrasound propagation: left to right.

Cavitation bubble clouds of comparable sizes can be successfully developed at the focus with and without the bone aberrators. In the initial stages of the treatment, large bubbles can form at the main beam location within the first few pulses. These cavitation bubbles can eventually form a larger cigar-shaped bubble cloud at the location of the main beam as a larger region of the target tissue is fractionated. Examples are shown in FIG. 6.

In the presence of the bone obstacles, small cavitation nuclei can also be observed near locations where the secondary lobes were the highest. In some embodiments, no bubbles will be generated in the secondary lobes when using 1-2 cycle pulses. However, as treatment progresses, these marginal bubbles do not become part of a cloud and will be pushed away by radiation force, eventually collapsing on their own within the first 1000 to 2000 pulses of therapy.

Figure 7:
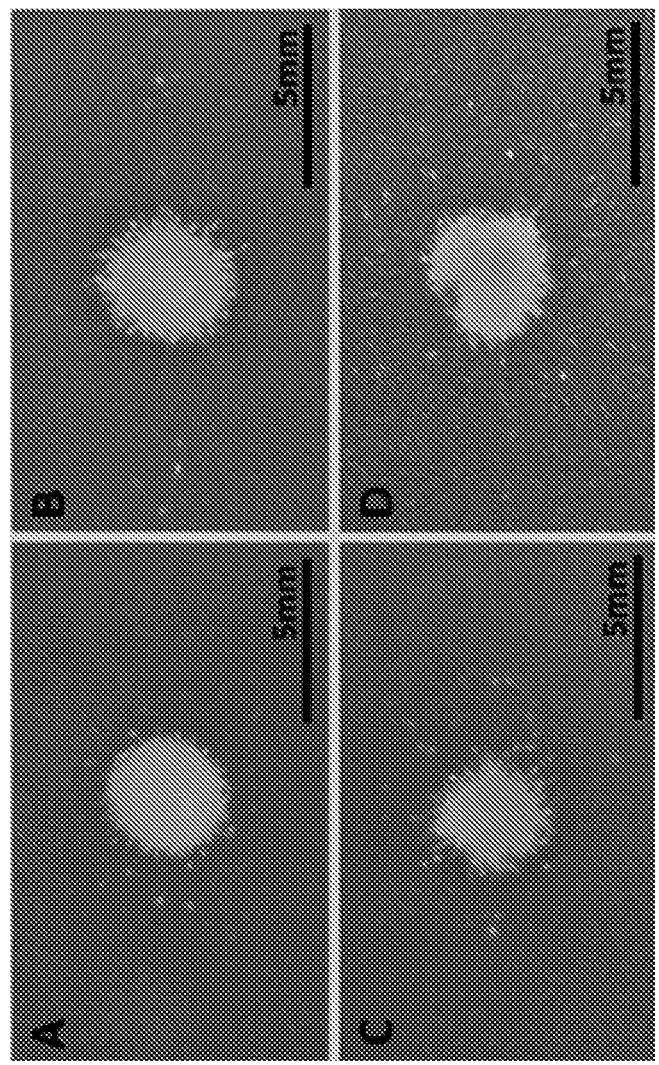
FIG. 7 illustrates transversal lesion patterns: (A) in free field, (B) with the rib phantom positioned at 8 cm before the transducer's geometric focus, (C) with the rib phantom at 4 cm and (D) with porcine ribs positioned at 8 cm. Lesions correspond to the visually clear areas surrounded by the darker background color of the RBC layer. Collateral damage was defined as the sum of all damage spots detected outside of the continuous portion of the main lesion.

In experimentation, lesions were successfully created at the focus of the transducer in all cases. A total of 87 lesions were created in tissue phantoms: 22 reference lesions were generated under free field conditions, 45 lesions were created through the polycarbonate rib phantom and 20 lesions through the porcine ribs. Morphology of the transversal plane from several representative lesions is shown in FIG. 7. A circular main lesion was observed in all treatment cases A-D, with collateral damage occurring in the form of a few sporadic points within a ring shaped zone around the main lesion area. In treatments through the bone aberrators, minor damage spots were observed at the locations where the secondary lobes were the highest, but no significant fractionation areas were observed outside the main lesion.

Figure 8:
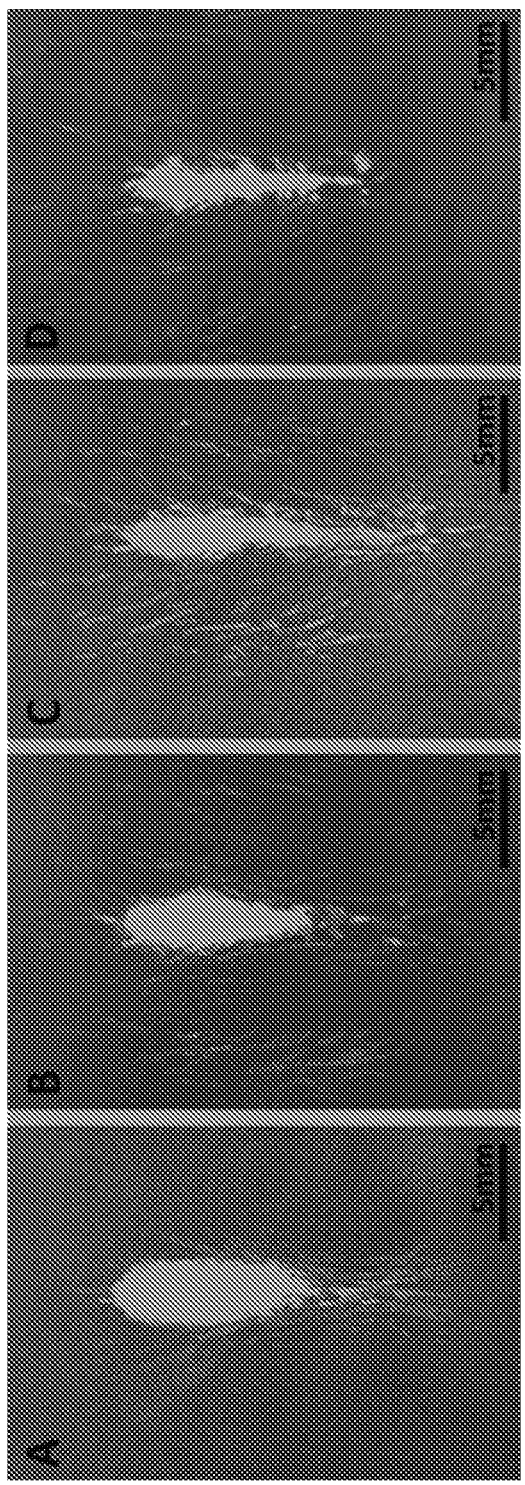
FIG. 8 shows representative longitudinal plane lesions (A) in free field, (B) with the rib phantom at 8 cm (C) with the rib phantom at 4 cm and (D) with porcine ribs positioned at 8 cm. The trailing path created by the translation of marginal bubble nuclei was the cause of most of the collateral effects seen on the longitudinal plane. Ultrasound propagation: top to bottom.

Longitudinal plane lesions were generated along the plane where secondary lobes were observed (i.e.: perpendicular to the orientation of the rib obstacles). A cigar-shaped main lesion was created in all treatments, with incompletely fractionated areas in the form of thin damage streaks at the tail of the main lesion (See FIG. 8). Lesions generated through the bone aberrators also displayed damage streaks on both sides of the main lesion, consistent with locations where the temporary marginal nuclei were observed during imaging. But as with the transversal plane treatments, no significant lesion development occurred outside the main beam region.

Figure 9:
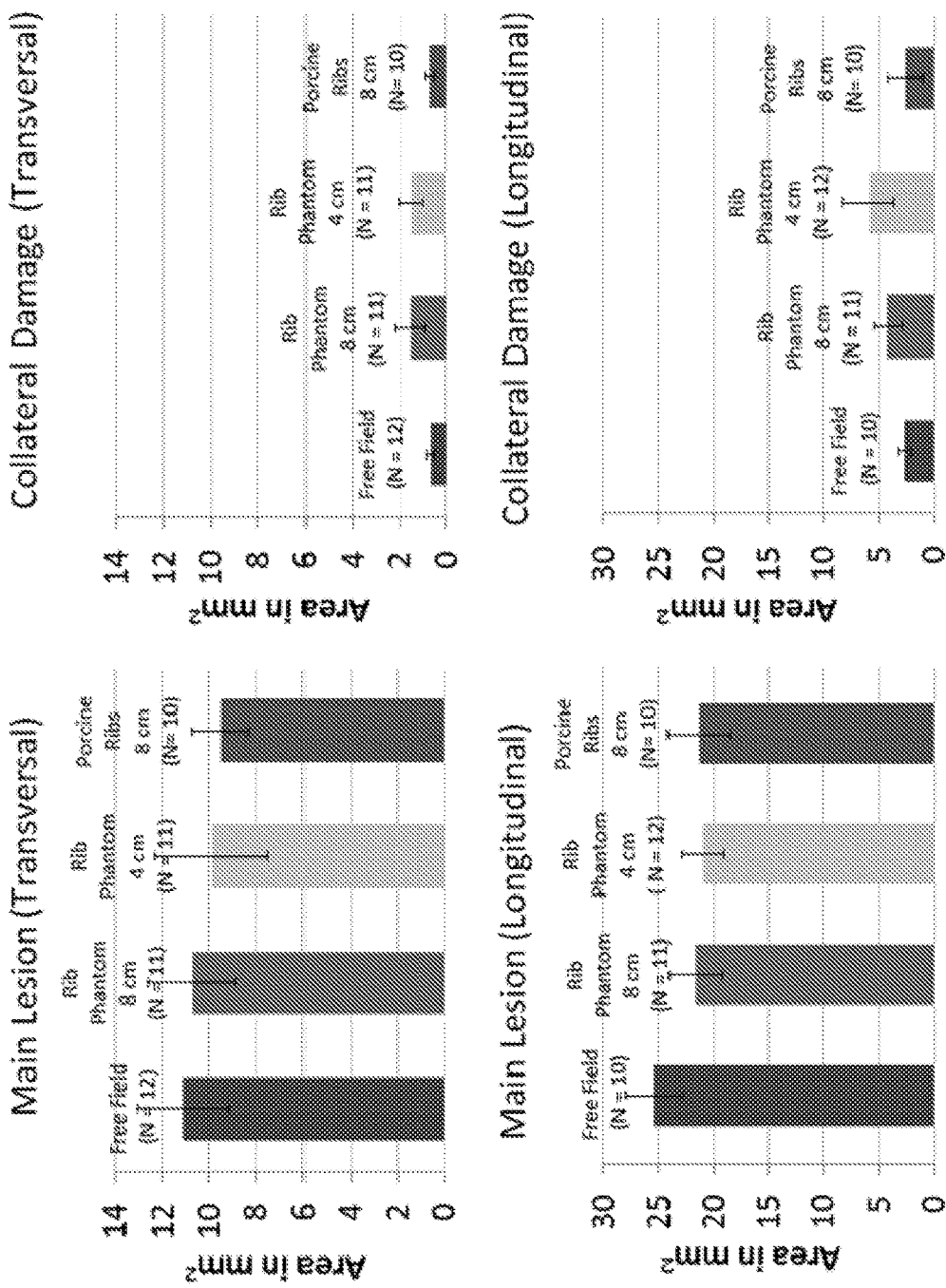
FIG. 9 illustrates average lesion dimensions and collateral damage on the transversal and longitudinal plane of lesions generated in free field and through the rib aberrators. Error bars correspond to plus or minus one standard deviation for each set of data.
Figure 10:
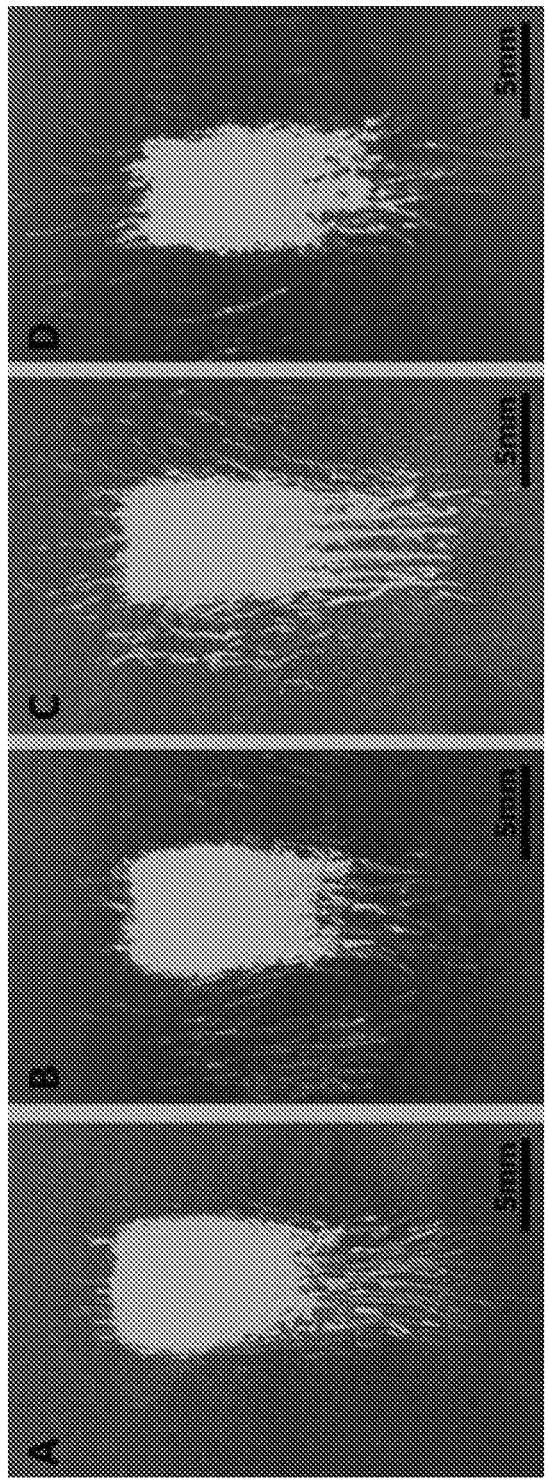
FIG. 10 shows lesions created by applying 5 adjacent treatments separated by 1 mm, covering a total zone of approximately 7×10 mm. (A) in free field, (B) with the rib phantom at 8 cm (C) with the rib phantom at 4 cm and (D) with porcine ribs positioned at 8 cm. Ultrasound propagation: top to bottom.

In a more quantitative point of view, focal lesion areas generated through the rib aberrators were comparable to within a standard deviation of the lesion areas created in free field, although the mean lesion sizes generated through the aberrators were slightly smaller (See FIG. 9). Considering mean lesion dimensions in both transversal and longitudinal planes, the largest lesions were generated in free field conditions while the smallest lesions were obtained through the porcine ribs.

In experiments, the collateral damage created through the porcine ribs was minimal and not statistically significant in comparison to that observed in free field lesions (Transversal: N=10/p-value=0.92; Longitudinal: N=10/p-value=0.7). Higher amount of collateral damage from marginal bubble nuclei was observed in lesions created through the rib phantom, particularly when the phantom was placed closer to the focus (4 cm).

In actual treatment scenarios, a region larger than a single focal size should be ablated. In some embodiments, lesions comprising of multiple focal spots separated from one another can be created to generate composite lesions through the bone aberrators. As with the single focus treatments, comparable fractionated areas can be created in all cases; resulting lesion development is well confined and limited to the focal zone while collateral damage from secondary lobes consisted of thin streaks caused by the translation of marginal bubble nuclei.

Bone aberrators can significantly distort the focal profile primarily in the form of increased secondary lobes at the expense of a reduced main beam in comparison to free field measurements (i.e., no intervening bone aberrators). In the case of ribs, the formation of secondary lobes is primarily a consequence of the distribution of the solid bone obstacles of the ribs, which together act as an acoustic mask, effectively creating an aperture with active elements radiating from the transcostal gaps between the solid obstacles. While the relative location of these secondary lobes (in this case grating lobes) may change depending on the spatial pattern of blockage caused by the distribution of the rib bones, the shape of the main beam remains the same with and without the presence of rib obstacles. The shape and half-maximum width of the main beam are not appreciably changed with the introduction of the rib aberrators. In the presence of skull in the ultrasound pathway, the shape and position of the main beam may change.

Histotripsy therapy can be used to generate precise lesions through the ribs or other bone aberrators as long as the focal pressure main beam is above the cavitation cloud initiation threshold while secondary lobes are below the threshold. Supporting this premise, cavitation bubble clouds of similar sizes were generated through the ribs, and despite the high secondary lobes introduced by the rib aberrators, the formation of a full bubble cloud was limited to the main beam, which was also the only location where a lesion successfully developed. Temporary cavitation bubbles were observed to form at the locations of secondary lobes during the initial stages of treatment through the rib aberrators, but these bubbles did not form a cloud, eventually collapsing on their own, pushed away by radiation force. This is evidenced by the collateral damage patterns observed in the phantoms, which comprised of peripheral spots or streaks not comparable to the central main lesion.

In clinical applications requiring a larger volume to be ablated, lesions with multiple foci can be generated by mechanically sweeping the focus of the transducer or by electronic focal steering if a phase array is used. As ablated regions increase in size, collateral damage caused by secondary lobes would become even less relevant relative to the total size of the lesion.

In the experiment, although the main lesion dimensions generated with and without the rib aberrators were comparable when accounting standard deviation ranges, the mean area of lesions obtained through the rib aberrators was smaller relative to free field lesions. It should be pointed out that while all lesions were generated at similar focal peak rarefactional pressure levels, (13-15 MPa) peak compressional pressures were observed to vary more significantly, with measurements differing by as much as 10 MPa in comparison to free field.

While cavitation threshold pressures cannot be measured in-vivo, histotripsy therapy at or near bubble cloud threshold levels is still feasible since cavitation bubble clouds can be readily monitored using conventional ultrasound imagers, allowing the operator to be aware of when and where the threshold has been reached anywhere within a given region of interest. In an in-vivo scenario, the operator would start the treatment from low acoustic power settings and gradually increase power levels until a cavitation bubble cloud is imaged at the focal spot. Once a bubble cloud is created at the focus, treatment could then proceed at that power level, confining the bubble cloud to the location of the main beam and preventing secondary lobes from reaching the cavitation threshold. In the event that secondary lobes do reach the cavitation threshold, the operator can reduce the power levels under ultrasound imaging until only the bubble cloud at the focus remains.

In addition, because cavitation bubble clouds can be initiated at arbitrarily low duty cycles—even single pulses— as long as enough pressure is available at the focus, the likelihood of inducing thermal effects in overlying tissues can be drastically reduced with the pulsed ultrasound regime used in histotripsy therapy. In this study for example, the effective sonication duty cycle applied to achieve a bubble cloud was less than 0.07% in all treatments, which is a negligible value in terms of HIFU therapy standards. This could allow transcostal therapy to be performed using simple single element transducers with a significantly better tolerance against bone overheating effects, without necessarily requiring phased array designs in order to sonicate between intercostal spaces.

The rib or bone aberrators can significantly attenuate the peak focal pressure and introduce high secondary lobes in the focal profile. Treatment can be conducted by adjusting the input voltage of the transducer such that the peak rarefactional pressures are at similar levels to free field conditions. Despite the significant secondary lobes, cavitation bubble clouds can be generated at the main beam locations, resulting in lesions comparable in size to those created under free field conditions. Collateral damage from secondary lobes can be limited to damage spots caused by temporary cavitation bubbles that fail to coalesce into a cloud.

The threshold nature of the bubble cloud initiation in histotripsy therapy appears to confer it a good amount of robustness in the presence of high secondary lobes introduced by rib or bone aberrators. This characteristic, coupled with the non-thermal nature of the treatment, suggest that histotripsy therapy is a useful non-invasive tissue ablation modality for transcostal surgical applications such as treatment for hepatic and pancreatic cancer.

In some embodiments, a method of treating tissue with ultrasound energy comprises positioning a focus of a histotripsy transducer on a target tissue, delivering histotripsy energy from the histotripsy transducer through a bone aberrator, forming a histotripsy bubble cloud on the focus, and preventing the formation of secondary histotripsy bubble clouds without implementing an aberration correction algorithm.

In another embodiment, a method of treating tissue with ultrasound energy comprises positioning a focus of a histotripsy transducer on a target tissue, delivering histotripsy energy from the histotripsy transducer through a bone aberrator, and increasing a power level of the histotripsy transducer until a histotripsy bubble cloud develops at the focus.

In yet another embodiment, a method of treating tissue with ultrasound energy is provided, comprising positioning a focus of a histotripsy transducer on a target tissue, delivering histotripsy energy from the histotripsy transducer through a bone aberrator, forming a histotripsy bubble cloud on the focus, observing formation of a secondary histotripsy bubble cloud positioned away from the focus, and decreasing a power level of the histotripsy transducer to eliminate the secondary histotripsy bubble cloud.

In another embodiment, a method of treating tissue with ultrasound energy is provided, comprising delivering histotripsy energy from the histotripsy transducer through a bone aberrator, forming a histotripsy bubble cloud on a focus of the histotripsy transducer, forming a secondary histotripsy bubble cloud away from the focus of the histotripsy transducer, and decreasing a power level of the histotripsy transducer to eliminate the secondary histotripsy bubble cloud.

As for additional details pertinent to the present invention, materials and manufacturing techniques may be employed as within the level of those with skill in the relevant art. The same may hold true with respect to method-based aspects of the invention in terms of additional acts commonly or logically employed. Also, it is contemplated that any optional feature of the inventive variations described may be set forth and claimed independently, or in combination with any one or more of the features described herein. Likewise, reference to a singular item, includes the possibility that there are plural of the same items present. More specifically, as used herein and in the appended claims, the singular forms "a," "and," "said," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise herein, all technical and scientific terms used herein have the same meaning as commonly understood by one of ordinary skill in the art to which this invention belongs. The breadth of the present invention is not to be limited by the subject specification, but rather only by the plain meaning of the claim terms employed.

What is claimed is:

1. A method of treating tissue with ultrasound energy, comprising:
   positioning a focus of an ultrasound transducer on a target tissue;
   delivering at least one ultrasound pulse from the ultrasound transducer though a bone aberrator, the at least one ultrasound pulse having a focal pressure above a cavitation initiation threshold of the target tissue;
   forming a cavitation bubble cloud on the focus with the at least one ultrasound pulse; and
   in the event that a secondary cavitation bubble cloud develops away from the focus due to the bone aberrator, decreasing a power level of the ultrasound transducer until the secondary bubble cloud disappears.

2. The method of claim 1, further comprising treating the target tissue with the cavitation bubble cloud.

3. The method of claim 2, wherein treating the target tissue comprises ablating the target tissue.

4. The method of claim 1, further comprising imaging the focus with an ultrasound imaging system.

5. The method of claim 1, further comprising damaging the target tissue at the focus.

6. The method of claim 1, wherein delivering the at least one ultrasound pulse comprises delivering at least one short (<20 μsec), high pressure (peak negative pressure >10 MPa) shockwave ultrasound pulse at a duty cycle <5%.

7. The method of claim 1, wherein the bone aberrator comprises a rib cage.

8. The method of claim 1, wherein the bone aberrator comprises a skull.

9. The method of claim 1, wherein the bone aberrator comprises a pelvic bone.

10. The method of claim 1, further comprising:
    adjusting a position of the focus to a different portion of the target tissue;
    delivering at least one ultrasound pulse from the ultrasound transducer through the bone aberrator; and
    forming a cavitation bubble cloud on the focus at the different portion of the target tissue.

11. The method of claim 1, wherein delivering at least one ultrasound pulse comprises delivering a single ultrasound pulse.

12. The method of claim 1, wherein the ultrasound transducer comprises a histotripsy transducer.

13. The method of claim 1, wherein the at least one ultrasound pulse comprises at least one histotripsy pulse.

14. The method of claim 1, wherein the cavitation bubble cloud comprises a histotripsy bubble cloud.

15. The method of claim 1, wherein the cavitation initiation threshold comprises a histotripsy cavitation initiation threshold.

* * * * *